(12) United States Patent
Choi et al.

(10) Patent No.: US 12,213,896 B2
(45) Date of Patent: Feb. 4, 2025

(54) METHOD AND APPARATUS FOR ENHANCING OPERATION OF LEG PROTHESIS

(71) Applicant: UNIVERSITY OF CENTRAL FLORIDA RESEARCH FOUNDATION, INC., Orlando, FL (US)

(72) Inventors: Hwan Choi, Orlando, FL (US); Gabriel Rios Carbonell, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 404 days.

(21) Appl. No.: 17/632,024

(22) PCT Filed: Aug. 3, 2020

(86) PCT No.: PCT/US2020/044726
§ 371 (c)(1),
(2) Date: Feb. 1, 2022

(87) PCT Pub. No.: WO2021/022248
PCT Pub. Date: Feb. 4, 2021

(65) Prior Publication Data
US 2022/0265442 A1    Aug. 25, 2022

Related U.S. Application Data

(60) Provisional application No. 62/881,648, filed on Aug. 1, 2019.

(51) Int. Cl.
*A61F 2/60* (2006.01)
*A61F 2/66* (2006.01)
(Continued)

(52) U.S. Cl.
CPC ........ *A61F 2/60* (2013.01); *A61F 2002/5072* (2013.01); *A61F 2002/5093* (2013.01);
(Continued)

(58) Field of Classification Search
CPC ................ A61F 2/60; A61F 2002/5072; A61F 2002/5093; A61F 2002/607;
(Continued)

(56) References Cited

U.S. PATENT DOCUMENTS 2,652,570 A * 9/1953 Sargeson ................ A61F 2/588
623/63
9,913,738 B1 * 3/2018 Fikes ........................ A61F 2/70
(Continued)

FOREIGN PATENT DOCUMENTS

WO    2019021126 A1    1/2019

OTHER PUBLICATIONS

PCT/US2020/044726, PCT Search Report & Written Opinion, mailed Jan. 28, 2021, 12 pages.
(Continued)

*Primary Examiner* — Bruce E Snow
(74) *Attorney, Agent, or Firm* — Timothy H. Van Dyke; Wolter Van Dyke; Davis, PLLC

(57) ABSTRACT

A method and apparatus for enhancing the operation of leg prothesis is provided. The apparatus includes a cable configured to be attached to the leg prosthesis worn by a subject to move through a plurality of gait phases. The apparatus also includes a module configured to be mounted to the leg prosthesis. The module includes a tension spring configured to engage the cable to maintain tension in the cable. The module also includes a locking mechanism configured to lock a position of the tension spring and maintain a length of the cable defined between the module and the leg prosthesis during a first gait phase of the plurality of gait phases.

(Continued)

The locking mechanism is further configured to unlock the position of the tension spring to permit variation of the length of the cable during a second gait phase of the plurality of gait phases.

22 Claims, 11 Drawing Sheets

(51) Int. Cl.
 *A61F 2/50* (2006.01)
 *A61F 2/68* (2006.01)
 *A61F 2/70* (2006.01)

(52) U.S. Cl.
 CPC . *A61F 2002/607* (2013.01); *A61F 2002/6614* (2013.01); *A61F 2002/6836* (2013.01); *A61F 2002/6854* (2013.01); *A61F 2002/701* (2013.01)

(58) Field of Classification Search
 CPC ...... A61F 2002/6614; A61F 2002/6836; A61F 2002/6854; A61F 2002/701
 See application file for complete search history.

(56) References Cited

U.S. PATENT DOCUMENTS

| | | |
|---|---|---|
| 2010/0185301 A1 | 7/2010 | Hansen et al. |
| 2012/0283745 A1 | 11/2012 | Herr et al. |
| 2013/0046218 A1* | 2/2013 | Wiggin .................. A61F 5/0127 602/16 |
| 2015/0265425 A1 | 11/2015 | Aagaah et al. |

OTHER PUBLICATIONS

Choi, Hwan et al., "Gastrocnemius operating length with ankle foot orthoses in cerebral palsy", Prosthetics and Orthotics International, 2017, vol. 41, No. 3, pp. 247-284.

Collins, Steven H. et al., "Reducing the energy cost of human walking using an unpowered exoskeleton", Nature, Jun. 11, 2015, vol. 522, No. 7555, pp. 212-215.

Fey, Nicholas P. et al., "The influence of energy storage and return foot stiffness on walking mechanics and muscle activity in below-knee aputees", Clinical Biomechanics, 2011, vol. 26, pp. 1025-1032.

Folz, Alexander J., Design of a Passive Ankle Prosthesis with Energy Return That Increases with Increasing Walking Velocity, Master's Theses (2009-), 2017, vol. 448, 99 pages.

Malcolm et al., "The influence of push-off timing in a robotic anke-foot prosthesis on the energetics and mechanics of walking", Journal of NeuroEngineering and Rehabilitation, 2015, vol. 12, No. 21, 15 pages.

Ossur Dynamic Solutions: https://www.ossur.com/prosthetic-solutions/products/dynamic-solutions; downloaded from Internet Apr. 4, 2022, 2 pages.

Ottobockus: https://www.ottobockus.com/prosthetics/lower-limb-prosthetics/solution-overview/harmony-below-knee-vacuum-system/; Ottobock: Harmony below-knee vacuum prosthesis, downloaded from Internet Apr. 4, 2022, 4 pages.

Silverman, Anne K. et al., "Muscle and prosthesis contributions to amputee walking mechanics: A modeling study", Journal of Biomechanics, Jun. 2, 2012, vol. 45, pp. 2271-2278.

Ventura, Jessica D. et al., "The effect of prosthesis ankle energy storage and return properties on muscle activity in below-knee amputee walking", Gait & Posture, Feb. 2011, vol. 33, issue 2, pp. 220-226 Abstract Only.

\* cited by examiner

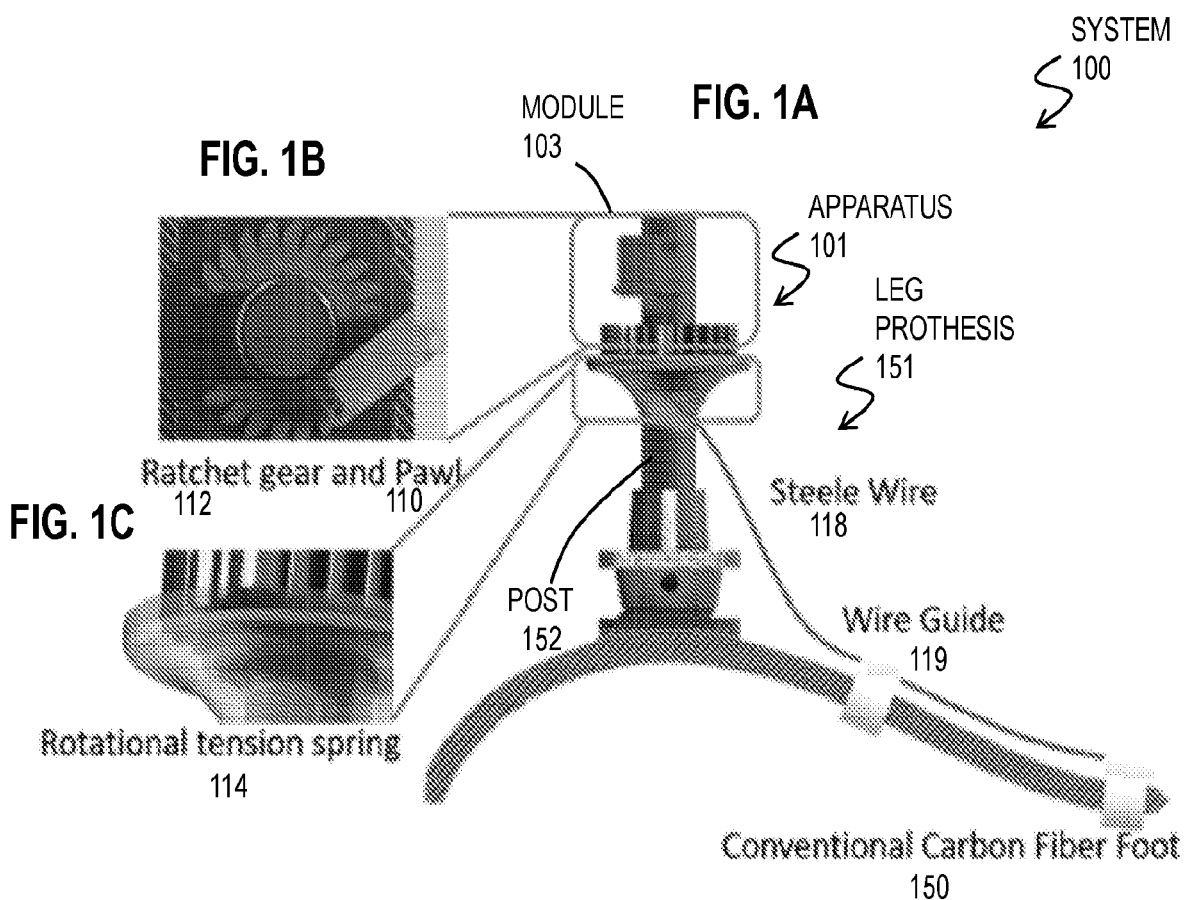

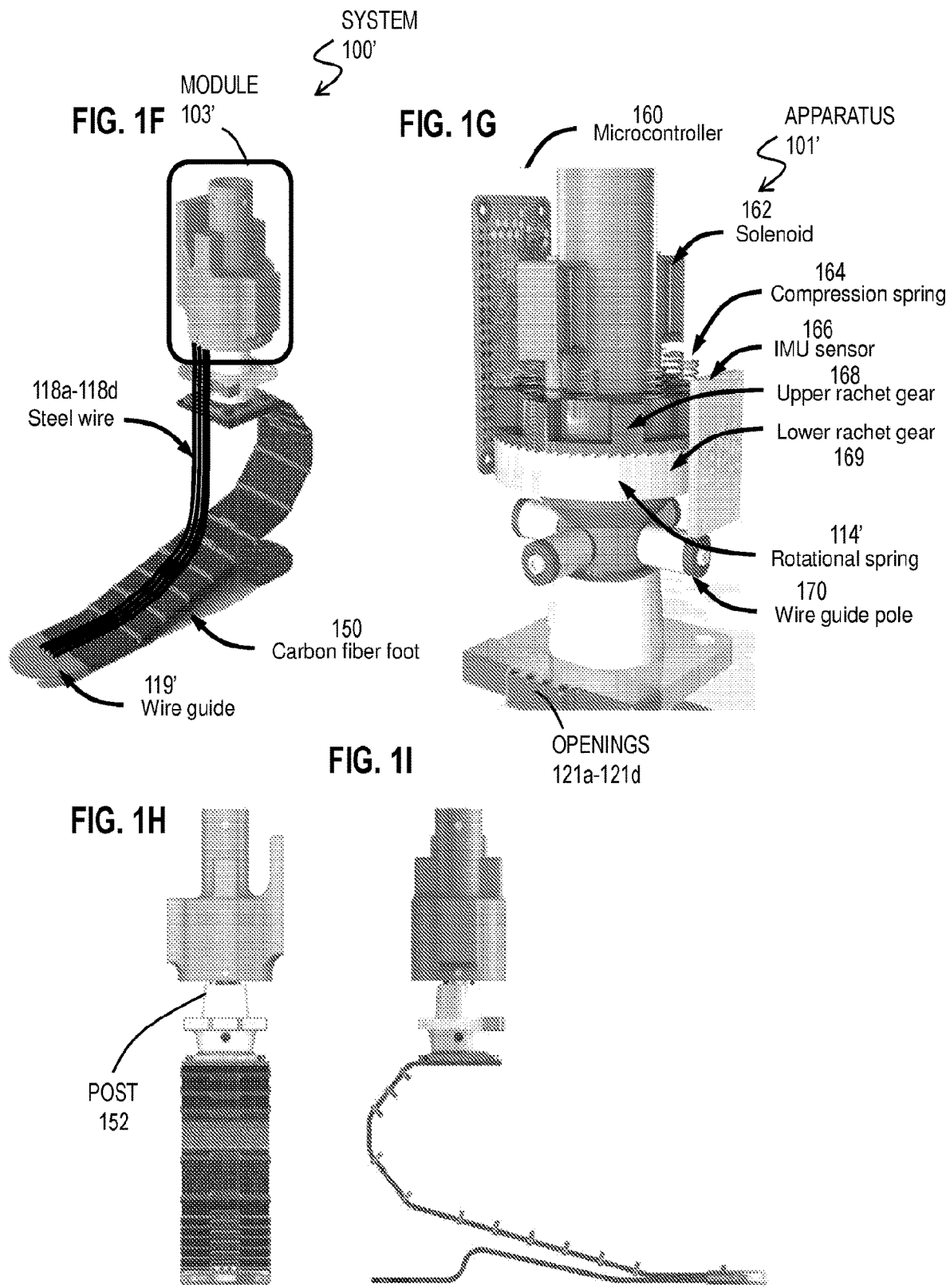

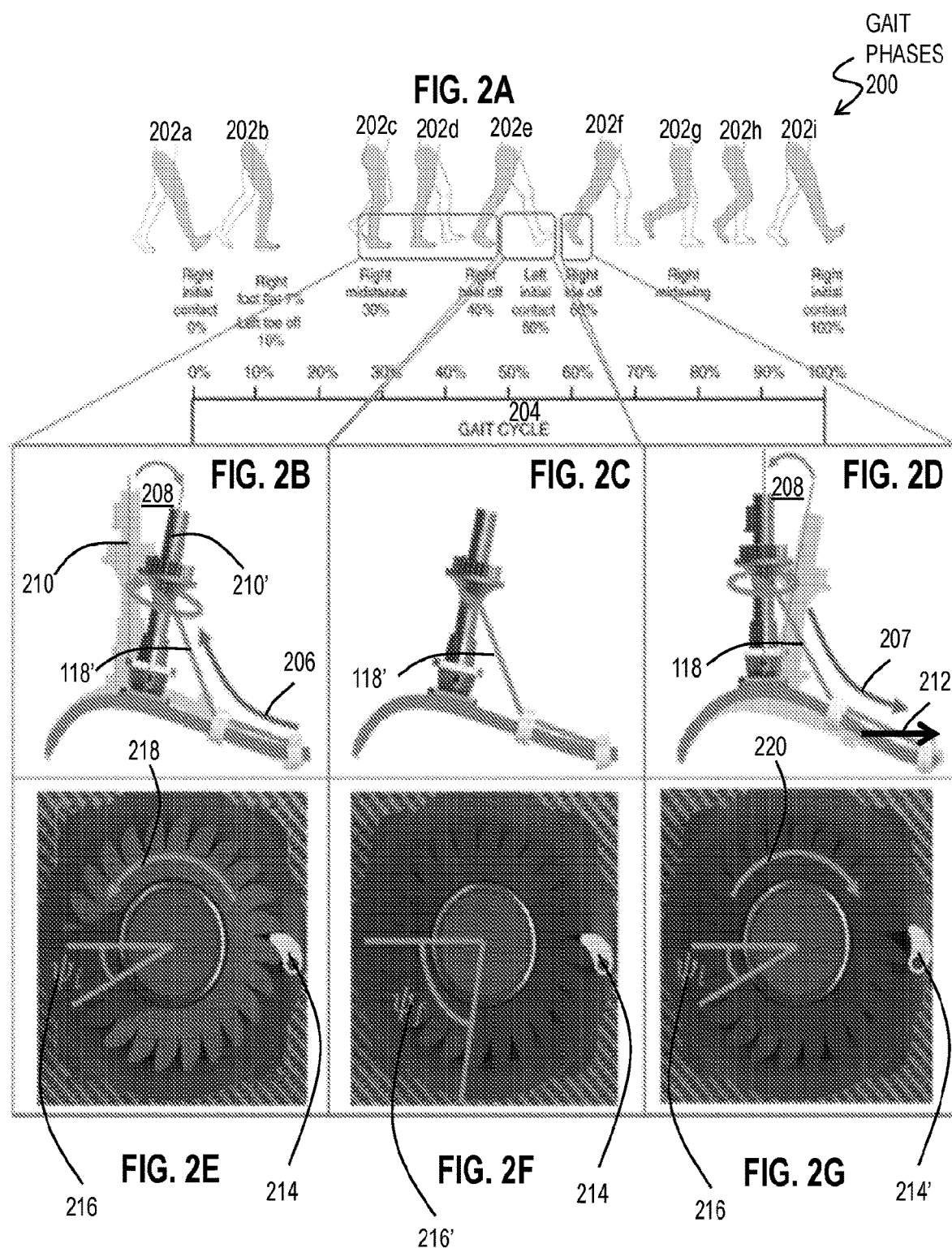

$\theta = 10°$, dorsiflexion, $20°$, dorsiflexion
$l_i = 331mm$ ($0°$ dorsiflexion)
206

$l_f = 320mm$ ($10°$ dorsiflexion), $307mm$ ($20°$ dorsiflexion)

$l_i = 331mm$ ($0°$ dorsiflexion)
207

Wire retract

Ratchet Gear Engaged

Wire release 218
216
216'
$\psi_i = 0°$ ($0°$ dorsiflexion), $\psi_f = 41°$ ($10°$ dorsiflexion), $87°$ ($20°$ dorsiflexion)

220
216
$\psi_i = 0°$ ($0°$ dorsiflexion),

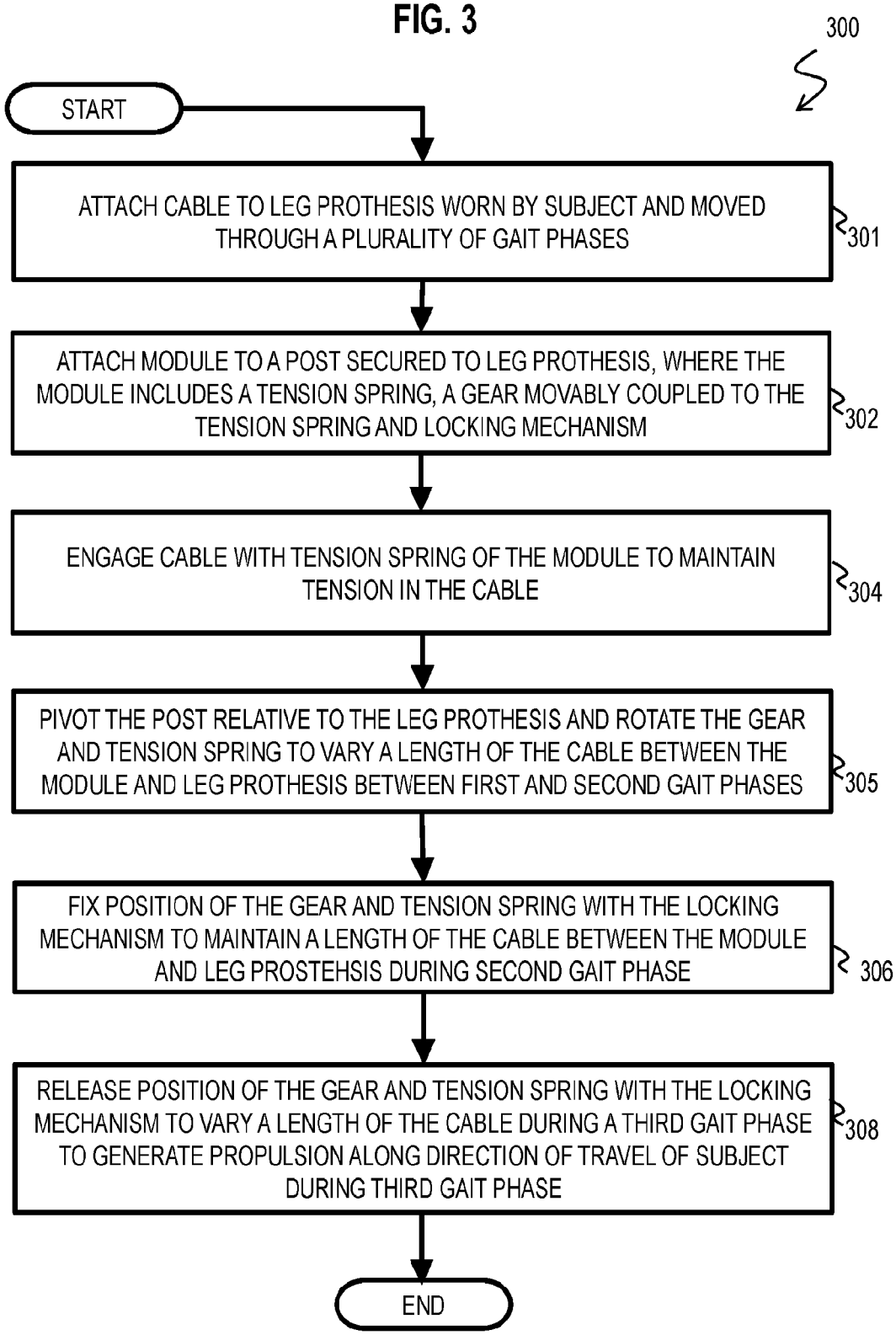

METHOD AND APPARATUS FOR ENHANCING OPERATION OF LEG PROTHESIS

CROSS REFERENCE TO RELATED APPLICATIONS

This application claims benefit of Provisional Application No. 62/881,648, filed Aug. 1, 2019, the entire contents of which is hereby incorporated by reference as if fully set forth herein, under 35 U.S.C. § 119(e).

BACKGROUND

Over 1.6 million people in the United States are living with lower limb amputation. This number is rising and is expected to double by 2050. Transtibial amputation, or below-knee amputation, has multiple disadvantages due to the loss of most of the calf muscle. Calf muscles, particularly the gastrocnemius and soles muscles, play an important role in supporting the body and propelling it forward.

SUMMARY

Passive ankle protheses are widely available due to having an affordable price, light weight and high durability. The key benefit of passive ankle prostheses is their use of energy recycling mechanisms, which enable individuals with transtibial amputation to walk efficiently and comfortably. For example, a common passive ankle prostheses made of carbon fiber stores energy by deforming its shape when people apply their weight during the mid and terminal stance of walking. The stored energy on the carbon fiber foot returns when the human body moves forward. However, conventional passive protheses cannot fully utilize this energy recycling mechanism due to an inability to control timing of energy release. An unimpaired individuals' gastrocnemius connects to the Achilles tendon. The gastrocnemius activates to hold the Achilles tendon in stretch during mid and terminal stance. The stretched Achilles tendon stores energy during this period that is released by the gastrocnemius muscle throughout an optimal time to maximize the propulsion and upward support of the body. The conventional passive prostheses mimic the energy recycling mechanism of the gastrocnemius and Achilles tendon. However, there is no control over energy release timing and the stored energy of the carbon fiber foot returns before the terminal stance when the body actually requires propulsion. This leads to energy being used only for upward support. As a result, individuals with lower limb amputation require extra musculature effort to be recruited to employ an appropriate gait pattern.

The inventors of the present invention developed a real-time adjustable energy releasing mechanism to overcome one or more drawbacks of conventional leg prostheses. For example, the real-time adjustable energy releasing mechanism allows people with lower limb amputation to have a customized release timing throughout varied walking conditions and speeds. The real-time adjustable energy releasing mechanism can be easily installed to already possessed passive prostheses, which would allow people with lower limb amputation to reduce the time, effort, and cost of getting a new prescription and purchasing a new prosthesis. The real-time adjustable energy release mechanism enables the control of energy timing by holding the passively stored energy from the carbon fiber foot and releasing it at appropriate times to propel the body forward. The main benefit of the module is that it can be installed to the existing ankle protheses without any modification.

The inventors recognized that ankle prostheses manage a large amount of force facilitating an individual walking in gait. The amount of force required changes based on individual needs such as weight and activity level. To compensate for the multiple settings of an ankle prosthesis, the embodiments of the system and apparatus are designed to capture the actual compression and deformation of the ankle prosthesis using a ratchet system that holds the deformation of the prosthetic foot until a proper timing is reached.

In one embodiment, an apparatus is provided including a cable configured to be attached to a leg prosthesis worn by a subject to move through a plurality of gait phases. The apparatus also includes a module configured to be mounted to the leg prosthesis. The module includes a gear configured to engage the cable to maintain tension in the cable. The module also includes a locking mechanism configured to lock a position of the gear and maintain a length of the cable defined between the module and the leg prosthesis during at least one first gait phase of the plurality of gait phases. The locking mechanism is further configured to unlock the position of the gear to permit variation of the length of the cable during at least one second gait phase of the plurality of gait phases.

In another embodiment, a method is provided including attaching a cable to a leg prosthesis worn by a subject and moved through a plurality of gait phases. The method further includes attaching a module to a post secured to the ankle prothesis, where the module comprises a tension spring, a gear movably coupled to the tension spring, and a locking mechanism. The method further includes engaging the cable with the gear of the module to maintain tension in the cable. The method further includes fixing, with the locking mechanism, a position of the gear and tension spring to maintain a length of the cable defined between the module and leg prosthesis during at least one first gait phase of the plurality of gait phases. The method further includes releasing, with the locking mechanism, the position of the gear and tension spring to vary the length of the cable during at least one second gait phase of the plurality of gait phases and generate propulsion along a direction of travel of the subject during the at least one second gait phase.

In another embodiment, a leg prosthesis is provided with an apparatus according to the above embodiment mounted thereon.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 1A is an image that illustrates an example of a side view of a system including a leg prothesis with an apparatus mounted thereon, according to an embodiment;

FIG. 1B is an image that illustrates an example of a top view of the gear and pawl of the apparatus of FIG. 1A, according to an embodiment;

FIG. 1C is an image that illustrates an example of a side view of the tension spring of the apparatus of FIG. 1A, according to an embodiment;

FIG. 1D is an image that illustrates an example of a front view of the system of FIG. 1A with a servo motor mounted to the leg prothesis, according to an embodiment;

FIG. 1F is an image that illustrates an example of a side perspective view of a system including a leg prothesis with an apparatus mounted thereon, according to an embodiment;

FIG. 1G is an image that illustrates an example of a sectional view of the module of the apparatus of FIG. 1F, according to an embodiment;

FIG. 1H is an image that illustrates an example of an end view of the system of FIG. 1F, according to an embodiment;

FIG. 1I is an image that illustrates an example of a side view of the system of FIG. 1F, according to an embodiment;

FIG. 2A is an image that illustrates an example of the gait phases of a walking gait, according to an embodiment;

FIG. 2B is an image that illustrates an example of a side view of the system of FIG. 1A moving from a third gait phase to a first gait phase, according to an embodiment;

FIG. 2C is an image that illustrates an example of a side view of the system of FIG. 1A during the first gait phase, according to an embodiment;

FIG. 2D is an image that illustrates an example of a side view of the system of FIG. 1A moving from the first gait phase to a second gait phase, according to an embodiment;

FIG. 2E is an image that illustrates an example of a top view of the gear of the system of FIG. 2B moving from the third gait phase to the first gait phase, according to an embodiment;

FIG. 2F is an image that illustrates an example of a top view of the gear of the system of FIG. 2C during the first gait phase, according to an embodiment;

FIG. 2G is an image that illustrates an example of a top view of the gear of the system of FIG. 2D moving from the first gait phase to the second gait phase, according to an embodiment;

FIG. 3 is a flow chart that illustrates an example method for using the mounting the apparatus to the system of FIG. 1A and using the system, according to an embodiment;

DETAILED DESCRIPTION

Figure 1E:
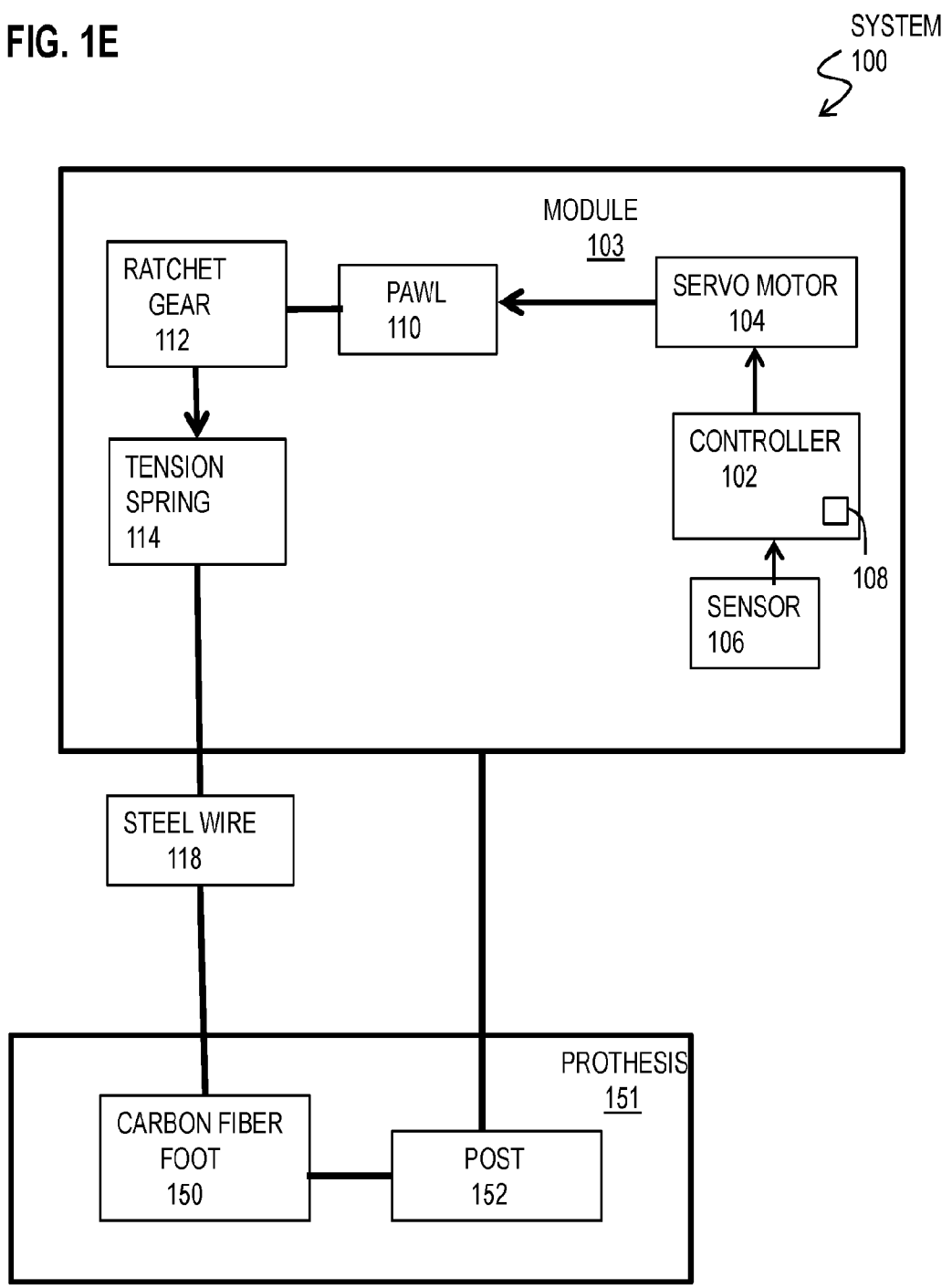
FIG. 1E is a block diagram that illustrates an example of the system of FIG. 1A, according to an embodiment.

A method and apparatus are described for enhancing the operation of leg prostheses and/or ankle protheses. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of enhancing the operation and functionality of leg prostheses and/or ankle prostheses. For purposes of this invention, "leg prostheses" means one or more artificial body parts to replace any part of the leg and/or foot of a subject (e.g. human or non-human) that is not present (e.g. amputated). In an example embodiment, the leg prostheses is one or more artificial body parts that replace one or more portions of the leg below the knee (e.g. for a transtibial amputation). In still other embodiments, the leg prostheses is one or more artificial body parts that replace one or more portions of the leg above the knee (e.g. for subjects with above knee amputation). In other embodiments, the embodiments are described below in the context of improving the timing of the release of energy at appropriate times (e.g. at the correct gait phase) during the operation of the leg protheses and/or ankle protheses. In still other embodiments, the invention is described in the context of prosthetics used to replace upper body limbs (e.g. hook prosthetic).

1. Overview

FIG. 1A is an image that illustrates an example of a side view of a system 100 including a leg prothesis 151 with an apparatus 101 mounted thereon, according to an embodiment. In an embodiment, the leg prothesis 151 is worn by a subject (e.g. human or non-human) to replace portions of the leg below the knee. In an example embodiment, the leg prothesis 151 is worn by a subject after a transtibial amputation. In some embodiments, the leg prothesis 151 is already worn by the subject and thus the invention is directed to the apparatus 101 which is mounted to the leg prothesis 151 in order to provide one or more advantages (e.g. improved control over energy release timing) during the operation of the leg prothesis 151. In one example embodiment, the apparatus 101 is a kit that can be installed to the existing leg prothesis 151 without any modification to the leg prothesis 151.

In an embodiment, the apparatus 101 includes a cable such as steel wire 118 that is attached to a foot portion (e.g. carbon fiber foot 150) of the leg prothesis 151. Although the carbon fiber foot 150 is depicted, this is merely one example of a foot portion of a leg prothesis and the embodiments of the invention can be employed with any foot portion of a leg prothesis. In one embodiment, one or more wire guides 119 are positioned along the carbon fiber foot 150 and the steel wire 118 is passed through the wire guides 119. In an example embodiment, the wire guides 119 are secured to the carbon fiber foot 150 by a clamp system that has a toe fitting to maintain the end of the wire 118 stationary with respect to a toe of the foot 150. In an example embodiment, the wire 118 at each end is attached to the carbon fiber foot 150 at one end and/or to a module 103 at an opposite end with one or more of epoxy, welds, cramps or weaving. In an example embodiment, the wire guides 119 are positioned along the carbon fiber foot 150 so that the steel wire 118 is passed through the wire guides 119 and along the carbon fiber foot 150 to a front portion of the carbon fiber foot 150 where the steel wire 118 is attached to the carbon fiber foot 150 (e.g. using at least one or more of epoxy, welds, cramps or weaving). In some embodiments, no wire guides 119 are provided and the steel wire 118 extends directly from the module 103 to the end of the carbon fiber foot 150. For purposes of this description, the "front portion" of the carbon fiber foot 150 is defined as the same portion of the carbon fiber foot 150 that faces a front side of a subject when wearing the leg prothesis 151 and/or faces a forward direction 212 of motion (FIG. 2D) of the subject.

In an embodiment, the apparatus 101 also includes a module 103 that is mounted to a post 152 of the leg prothesis 151. In an example embodiment, the module 103 is attached to the post 152 with a plurality (e.g. about 8) screws such as with some screws (e.g. about 4) on the top of the post 152 and other screws (e.g. about 4) on the bottom of the post 152. In other embodiments, the module 103 is attached to the post 152 using any means (e.g. adhesive, magnetic, etc.) other than screws, as appreciated by one of ordinary skill in the art. In an example embodiment, the post 152 includes threaded openings to which the screws will engage while providing clamping force, without damaging the existing prosthetic (e.g. see FIGS. 1F-1G). In an embodiment, the module 103 includes a tension spring 114 and ratchet gear 112 that is rotatably coupled with the tension spring 114. In one embodiment, the ratchet gear 112 engages the steel wire 118 to maintain tension (e.g. through the tension spring 114 rotatably coupled to the gear 112) in the steel wire 118. In an example embodiment, the ratchet gear 112 engages an opposite end of the steel wire 118 than the end of the steel wire 118 that is attached to the carbon fiber foot 150. FIG. 1C is an image that illustrates an example of a side view of the tension spring 114 of the apparatus 101 of FIG. 1A, according to an embodiment. In an example embodiment, the tension spring 114 is a rotational tension spring 114 that is configured to rotate based on retraction of the steel wire 118 into the module 103 to maintain a minimum level of tension in the steel wire 118. In an example embodiment, the steel wire 118 retracts and wraps around a base of the ratchet gear 112 as the ratchet gear 112 rotates.

In an embodiment, the module 103 also includes a locking mechanism that locks a position of the ratchet gear 112 and tension spring 114 and maintains a length of the steel wire 118 (e.g. defined between the module 103 and the carbon fiber foot 150) during a first gait phase (e.g. midstance gait phase and/or terminal gait phase). In an embodiment, the locking mechanism also unlocks a position of the ratchet gear 112 and tension spring 114 to permit variation of the length of the steel wire 118 during a second gait phase (e.g. toe off gait phase).

In one embodiment, the locking mechanism features teeth of a gear and a pawl. FIG. 1B is an image that illustrates an example of a top view of the ratchet gear 112 and pawl 110 of the apparatus 101 of FIG. 1A, according to an embodiment. In one embodiment, the gear 112 is movably coupled to the tension spring 114. In an example embodiment, where the tension spring 114 is a rotational tension spring 114, the gear 112 is a ratchet gear 112 that is rotatably coupled to the tension spring 114. In an embodiment, the ratchet gear 112 includes a plurality of teeth and the pawl 110 is configured to engage one of the teeth. In an example embodiment, when the pawl 110 engages teeth of the ratchet gear 112 it prevents the ratchet gear 112 from rotating in one direction and permits rotation in the opposite direction. In one embodiment, the pawl 110 is configured to engage the gear 112 to lock the position (e.g. in one direction) of the gear 112 and the tension spring 114 during the first gait phase to maintain the steel wire 118 length. In this embodiment, the pawl 110 is further configured to disengage the gear 112 to unlock the position of the gear 112 and the tension spring 114 during the second gait phase to permit variation of the steel wire 118 length.

In one embodiment, the locking mechanism further includes a servo motor 104 to cause the pawl 110 to disengage the gear 112 based on whether the subject walking gait is in the second gait phase. FIG. 1D is an image that illustrates an example of a front view of the system of FIG. 1A with the servo motor 104 mounted to the leg prothesis, according to an embodiment. In other embodiments, the apparatus 101 includes a sensor (not shown) that measures a current gait phase of the leg prothesis and transmits data indicating the current gait phase to the servo motor 104. In an example embodiment, the sensor is an inertial measurement unit (IMU) sensor (e.g. 9 degree of freedom IMU sensor) and/or coupled with a microcontroller to calculate the timing when the pawl 110 should be disengaged by determining when the current gait phase is the second gait phase. In this example embodiment, the servo motor 104 is configured to cause the pawl 110 to disengage the gear 112 based on a determination that the current gait phase indicated by the sensor data corresponds to the second gait phase.

FIG. 1E is a block diagram that illustrates an example of the system 100 of FIG. 1A, according to an embodiment. In an embodiment, the module 103 includes a microcontroller or controller 102, such as a computer system described below with reference to FIG. 4, or a chip set described below with reference to FIG. 5. A memory 108 of the controller 102 includes instructions to perform one or more steps of the method 300 based on the flowchart of FIG. 3. In an embodiment, the module 103 also includes a sensor 106 (e.g. IMU sensor) that is configured to measure data indicating the current gait phase of the leg prothesis 151 and to transmit the measured data to the controller 102. In an example embodiment, the controller 102 receives the data indicating the current gait phase of the leg prothesis 151 and compares the current gait phase with the second gait phase during which the pawl 110 is to disengage the gear 112 and tension spring 114. In an example embodiment, the second gait phase is stored in the memory 108 of the controller 102. In some embodiments, the controller 102 is integral with the servo motor 104.

FIG. 2A is an image that illustrates an example of the gait phases 200 of a walking gait, according to an embodiment. In an embodiment, the gait phases 200 have a percentage (%) value based on their phase in the gait cycle, where 0% is defined as right heel initial contact gait phase. In this embodiment, the gait phases 200 includes a 0% gait phase 202a based on initial right heel contact; a 10% gait phase 202b based on flat right foot; 30-40% gait phases 202c-202d based on right midstance; 50% gait phase 202e based on right heel off; 60% gait phase 202f based on right toe off; 80-90% gait phases 202g, 202h based on right foot swing and 100% gait phase 202i based on right initial contact. Although the 0% value is defined as the right heel initial contact gait phase, any of the gait phases can be used to define the 0% value.

FIG. 2B is an image that illustrates an example of a side view of the system 100 of FIG. 1A moving from a third gait phase (e.g. 30% gait phase 202c) to a first gait phase (e.g. 50% gait phase 202e), according to an embodiment. As depicted in FIG. 2B, the post 152 of the leg prothesis 151 is pivotally coupled to the carbon fiber foot 150 such that the post 152 rotates from a first axis 210 during the third gait phase over an angle 208 to a second axis 210' during the first gait phase. In an embodiment, the angle 208 is in a range from about 0 degrees to about 20 degrees and/or in a range from about 0 degrees to about 30 degrees. FIG. 2E is an image that illustrates an example of a top view of the gear 112 of the system 100 of FIG. 2B moving from the third gait phase to the first gait phase, according to an embodiment. As the post 152 rotates over the angle 208, the gear 112 and rotational tension spring 114 rotate in a counterclockwise direction 218 (FIG. 2E) so that the steel wire 118 retracts in direction 206 into the module 103 and the rotational tension spring 114 maintains tension in the steel wire 118. In an embodiment, a length of the steel wire 118 is shortened between the third gait phase and the first gait phase from about 331 millimeters (mm) to about 320 mm (e.g. 10 degree angle 208) and/or to about 307 mm (e.g. 20 degree angle 208), which corresponds to retraction length of the steel wire 118 of about 11 mm (e.g. 10 degree angle 208) and/or 24 mm (e.g. 20 degree angle 208). In an embodiment, the gear 112 and rotational tension spring 114 rotate in the counterclockwise direction 218 from an initial angle 216 (FIG. 2E) to a final angle 216' (FIG. 2F) as the system 100 moves from the third gait phase to the first gait phase. In an example embodiment, the initial angle 216 is about 0 degrees and the final angle 216' is about 41 degrees (e.g. about 10 degree angle 208) and/or about 87 degrees (e.g. about 20 degree angle 208) and thus the net rotation angle is about 41 degrees (e.g. about 10 degrees angle 208) and/or about 87 degrees (e.g. about 20 degree angle 208).

FIG. 2C is an image that illustrates an example of a side view of the system 100 of FIG. 2B during the first gait phase, according to an embodiment. During the second first phase (e.g. 50% gait phase 202e) the pawl 110 engages the ratchet gear 112 in an engaged position 214 (FIG. 2F) to lock the position of the ratchet gear 112 during the first gait phase and thus ensure that stored energy in the form of the retracted steel wire 118 length in the module 103 is not released. By engaging the gear 112, the pawl 110 prevents rotation of the gear 112 and tension spring 114 in a clockwise direction 220 opposite to the counterclockwise direction 218 which would be required for release of the stored energy from the steel wire 118 length retracted into the module 103. This overcomes a drawback of the conventional leg prothesis where the stored energy is released at or immediately after the first gait phase (e.g. 50% gait phase 202e) and provides upward force rather than propulsive force in a direction of travel. FIG. 2F is an image that illustrates an example of a top view of the gear 112 of the system 100 of FIG. 2C during the first gait phase, according to an embodiment. As depicted in FIG. 2F, the gear 112 and rotational tension spring 114 have rotated to the final angle 216' and are held at the final angle 216' during the first gait phase, based on the engagement of the gear 112 with the pawl 110.

FIG. 2D is an image that illustrates an example of a side view of the system 100 of FIG. 1A moving from the first gait phase (e.g. 50% gait phase 202e) to a second gait phase (e.g. 60% gait phase 202f), according to an embodiment. In an embodiment, the sensor 106 (FIG. 1E) measures the current gait phase of the leg prothesis and transmits data indicating the current gait phase to the controller 102. In one embodiment, the controller 102 compares the current gait phase with the second gait phase (e.g. stored in the memory 108 of the controller 102). Upon determining that the current gait phase corresponds to the second gait phase, the controller 102 transmits a signal to the servo motor 104 which in turn transmits a signal to the pawl 110 to cause the pawl 110 to disengage the gear 112. In an embodiment, after the pawl 110 disengages the gear 112 and rotational tension spring 114, the retracted length of the steel wire 118 is released in direction 207 which maintains proper tension in the wire 118. Additionally, as depicted in FIG. 2D, the post 152 rotates from being aligned with the axis 210' through the angle 208 back to the axis 210 during the moving from the first gait phase to the second gait phase. This advantageously provides propulsion along the direction of travel 212.

FIG. 2G is an image that illustrates an example of a top view of the gear 112 of the system 100 of FIG. 2C moving from the first gait phase to the second gait phase, according to an embodiment. As depicted in FIG. 2G, during the transition from the first gait phase to the second gait phase, the gear 112 and rotational tension spring 114 rotate in a clockwise direction 220 (e.g. opposite to counterclockwise direction 218 in FIG. 2E) from an initial angle 216' (FIG. 2F) to a final angle 216 (FIG. 2G). FIG. 2G further depicts the pawl 110 in a disengaged position 214' so that the gear 112 and rotational tension spring 114 can move in the clockwise direction 220. Note that the gear 112 and rotational tension spring 114 can move in the counterclockwise direction 218 with the pawl 110 engaging the gear 112 (FIG. 2E) but cannot move in the clockwise direction 220 unless the pawl 110 is disengaged from the gear 112. Although clockwise and counterclockwise direction are used herein, it should be noted that the directions could be reversed should that FIG. 2E could be rotating in the clockwise direction and FIG. 2G could be rotating in the counterclockwise direction, provided that the pawl was appropriately positioned.

Additionally, although the locking mechanism featuring the pawl 110, gear 112 and tension spring 114 are discussed herein, the embodiments of the present invention includes any locking mechanism that can be used to maintain a length of the steel wire 118 during the first gait phase and release a length of the steel wire 118 during the second gait phase. Thus, the locking mechanism is not limited to the depicted embodiments featuring a pawl 110, gear 112 and/or tension spring 114 in the module 103.

FIG. 1F is an image that illustrates an example of a side perspective view of a system 100' including the leg prothesis 151 with an apparatus 101' mounted thereon, according to an embodiment. FIG. 1H is an image that illustrates an example of an end view of the system 100' of FIG. 1F, according to an embodiment. FIG. 1I is an image that illustrates an example of a side view of the system 100' of FIG. 1F, according to an embodiment. In an embodiment, the apparatus 101' and module 103' is similar to the apparatus 101 and module 103 discussed above, with the exception of the details discussed herein. In an embodiment, a plurality (e.g. about 4 or in a range from about 2 to about 8) of steels wires 118a-118d are provided and extend between the carbon fiber foot 150 and the module 103'. In an embodiment, wire guides 119' guide the steel wires 118a-118d along the carbon fiber foot 150. In an example embodiment, the steel wires 118a-118d are attached to the carbon fiber foot 150 (e.g. front portion) using similar techniques as in the system 100.

FIG. 1G is an image that illustrates an example of a sectional view of the module 103' of the apparatus 101' of FIG. 1F, according to an embodiment. In an embodiment, a plurality of openings 121a-121d (e.g. about 4 or in a range from about 2 to about 8) are defined adjacent a base of the apparatus 101', where each opening 121 is configured to receive a respective steel wire 118. In another embodiment, a plurality of wire guide poles 170 are provided (e.g. about 4) where a respective steel wire 118 is directed from a respective opening 121 to a respective wire guide pole 170 and then to a respective portion (not shown) of a lower ratchet gear 169. In an example embodiment, the plurality of wire guide poles 170 separate the steel wires 118a-118d before they are attached to the lower ratchet gear 169 and thus advantageously ensure the wires 118a-118d are not tangled when they are attached to respective segments of the lower ratchet gear 169.

In an embodiment, the apparatus 101' includes a microcontroller 160 that is similar to the controller 102. In one embodiment, instead of the servo motor 104, the apparatus 101' includes a solenoid 162 that is communicatively coupled to the microcontroller 160. In one embodiment, the solenoid 162 is operatively connected to an upper ratchet gear 168 through a compression spring 164 and the upper ratchet gear 168 is configured to engage the lower ratchet gear 169 (e.g. teeth of upper ratchet gear 168 are configured to engage teeth of the lower ratchet gear 169). In an embodiment, the upper ratchet gear 168 and lower ratchet gear 169 rotate relative to each other in a first direction 218 when they are engaged and cannot rotate relative to each other in a second direction 220 opposite to the first direction 218 when they are engaged. In an embodiment, upon receiving a signal from the microcontroller 160 the solenoid 162 is configured to raise the upper ratchet gear 168 relative to the lower ratchet gear 169 (e.g. by releasing the compression spring 164 that maintains the upper and lower ratchet gears 168, 169 in contact). In an example embodiment, after raising the upper ratchet gear 168 relative to the lower ratchet gear 169, the lower ratchet gear 169 can rotate relative to the upper ratchet gear 168 in the second direction. In an example embodiment, the upper and lower ratchet gears 168, 169 each include a plurality of teeth around a circumference of the gears 168, 169 which engage to lock rotation of the gears 168, 169 with respect to each other in the second direction. This advantageously dissipates the stress of the locking mechanism over the plurality of teeth around the circumference of the gears 168, 169.

In another embodiment, the apparatus 101' includes an IMU sensor 166 that is similar to the sensor 106 that is communicatively coupled with the microcontroller 160 of FIG. 1E. In an example embodiment, at each gait phase the IMU sensor 166 transmits data (e.g. angle data) indicating the current gait phase to the microcontroller 160. In an example embodiment, the microcontroller compares this data with data in the memory 108 (e.g. the second gait phase). Based on this comparison, the microcontroller 160 determines whether to transmit the signal to the solenoid 162 to cause the upper ratchet gear 168 to rise relative to the lower ratchet gear 169 which subsequently causes the lower ratchet gear 169 to rotate in the second direction 220 and to release the plurality of steel wires 118a-118d.

Figure 2H:
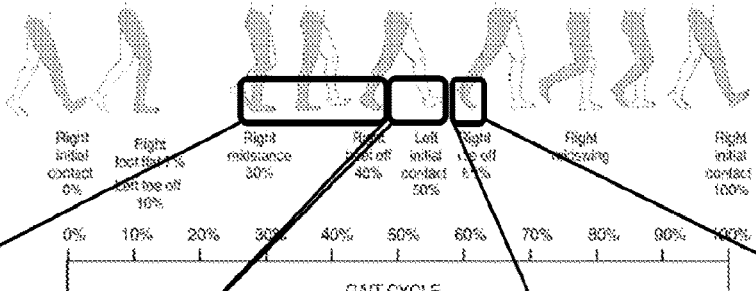
FIG. 2H is an image that illustrates an example of the gait phases of FIG. 2A, according to an embodiment.
Figure 2I:
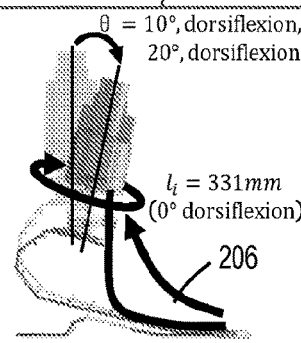
FIGS. 2I, 2L and 2O are images that illustrate an example of the system of FIG. 1F moving from a third gait phase to a first gait phase, according to an embodiment.

FIG. 2H is an image that illustrates an example of the gait phases 200 of FIG. 2A, according to an embodiment. FIGS. 2I, 2L and 2O are images that illustrate an example of the system 100' of FIG. 1F moving from a third gait phase (e.g. 30% gait phase 202c) to a first gait phase (e.g. 50% gait phase 202e), according to an embodiment. The system 100' moves from the third gait phase to the first gait phase in a similar manner as the system 100 discussed above with respect to FIGS. 2B, 2E, with the exception of the features discussed herein. As the post 152 rotates over the angle 208, the lower ratchet gear 169 rotates relative to the upper ratchet gear 168 in a counterclockwise direction 218 (FIG. 2O) so that the steel wires 118a-118d retract in direction 206 into the module 103' and the rotational tension spring 114' maintains tension in the steel wires 118a-118d. As previously discussed, each respective steel wire 118a-118d is attached to a respective portion of the lower ratchet gear 169 and each steel wire 118 is retracted around the lower ratchet gear 169. In an example embodiment, the lower ratchet gear 169 is rotatable relative to the upper ratchet gear 168 in the direction 218, since the teeth of the respective gears 168, 169 are oriented to permit rotation of the lower ratchet gear 169 relative to the upper ratchet gear 168 as the gears 168, 169 are engaged (e.g. by the compression spring 164). In an embodiment, the lower ratchet gear 169 and rotational tension spring 114' rotate in the counterclockwise direction 218 from an initial angle 216 (FIG. 2O) to a final angle 216' (FIG. 2P) as the system 100' moves from the third gait phase to the first gait phase.

Figure 2J:
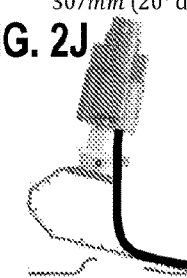
FIGS. 2J, 2M and 2P are images that illustrate an example of the system of FIG. 1F during the second first phase, according to an embodiment.
Figure 2K:
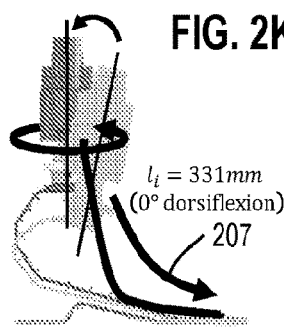
FIGS. 2K, 2N and 2Q are images that illustrate an example of the system of FIG. 1F moving from the first gait phase to the second gait phase, according to an embodiment.
Figure 2L:
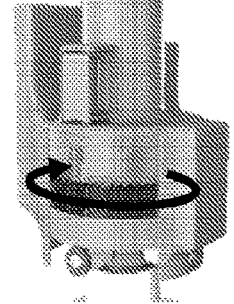
Figure 2M:
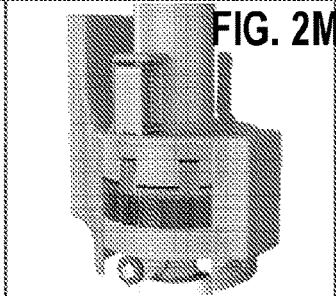
Figure 2N:
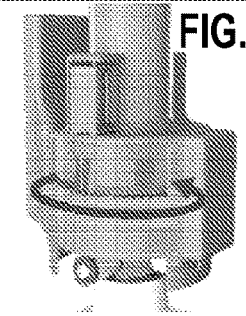
Figure 2O:
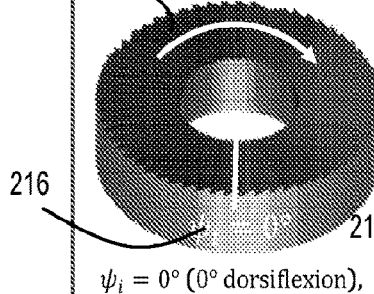
Figure 2P:
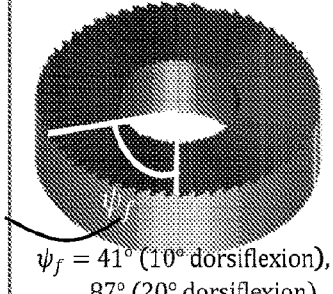

FIGS. 2J, 2M and 2P are images that illustrate an example of the system 100' of FIG. 1F during the first gait phase (e.g. 50% gait phase 202e), according to an embodiment. During the first gait phase (e.g. 50% gait phase 202e) the upper ratchet gear 168 engages the lower ratchet gear 169 (FIGS. 2M, 2P) to lock the position of the lower ratchet gear 169 during the first gait phase and thus ensure that stored energy in the form of the retracted steel wires 118a-118d length in the module 103' is not released. Through the compression spring 164, the upper ratchet spring 168 continuously engages the lower ratchet gear 169, and thus the upper ratchet gear 168 prevents rotation of the lower ratchet gear 169 and tension spring 114' in a clockwise direction 220 opposite to the counterclockwise direction 218 which would be required for release of the stored energy from the steel wires 118a-118d length retracted into the module 103'. As depicted in FIG. 2P, the lower ratchet gear 169 and rotational tension spring 114' have rotated to the final angle 216' ($\psi_f$ in FIG. 2P) and are held at the final angle 216' during the first gait phase, based on the engagement of the lower ratchet gear 169 with the upper ratchet gear 168.

Figure 2Q:
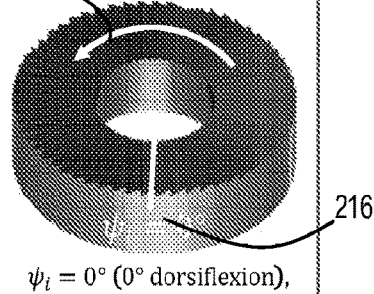

FIGS. 2K, 2N and 2Q are images that illustrate an example of the system 100' of FIG. 1F moving from the first gait phase (e.g. 50% gait phase 202e) to the second gait phase (e.g. 60% gait phase 202f), according to an embodiment. Upon determining that the current gait phase corresponds to the second gait phase, the microcontroller 160 transmits a signal to the solenoid 162 which in turn actuates the compression spring 164 to cause the upper ratchet spring 168 to rise relative to the lower ratchet gear 169 and disengage the lower ratchet gear 169. In an embodiment, after the upper ratchet gear 168 disengages the lower ratchet gear 169 and rotational tension spring 114', the retracted length of the steel wires 118a-118d are released in direction 207 which maintains proper tension in the wires 118a-118d. Additionally, as depicted in FIG. 2K, the post 152 rotates from being aligned with the axis 210' through the angle 208 back to the axis 210 during the moving from the first gait phase to the second gait phase. This advantageously provides propulsion along the direction of travel 212. FIG. 2Q is an image that illustrates an example of a top view of the lower ratchet gear 169 of the system 100' of FIG. 2K moving from the first gait phase to the second gait phase, according to an embodiment. As depicted in FIG. 2Q, during the transition from the first gait phase to the second gait phase, the lower ratchet gear 169 and rotational tension spring 114' rotate in a clockwise direction 220 (e.g. opposite to counterclockwise direction 218 in FIG. 2O) from an initial angle (FIG. 2P) to a final angle (FIG. 2Q). FIG. 2N further depicts the upper ratchet gear 168 in a disengaged position from the lower ratchet gear 169 so that the lower ratchet gear 169 and rotational tension spring 114' can move in the clockwise direction 220. Note that the lower ratchet gear 169 and rotational tension spring 114' can move in the counterclockwise direction 218 with the upper ratchet gear 168 engaging the lower ratchet gear 169 (FIGS. 2L, 2O) but cannot move in the clockwise direction 220 unless the upper ratchet gear 168 is disengaged (e.g. with the compression spring 164) from the lower gear 169.

Figure 1J:
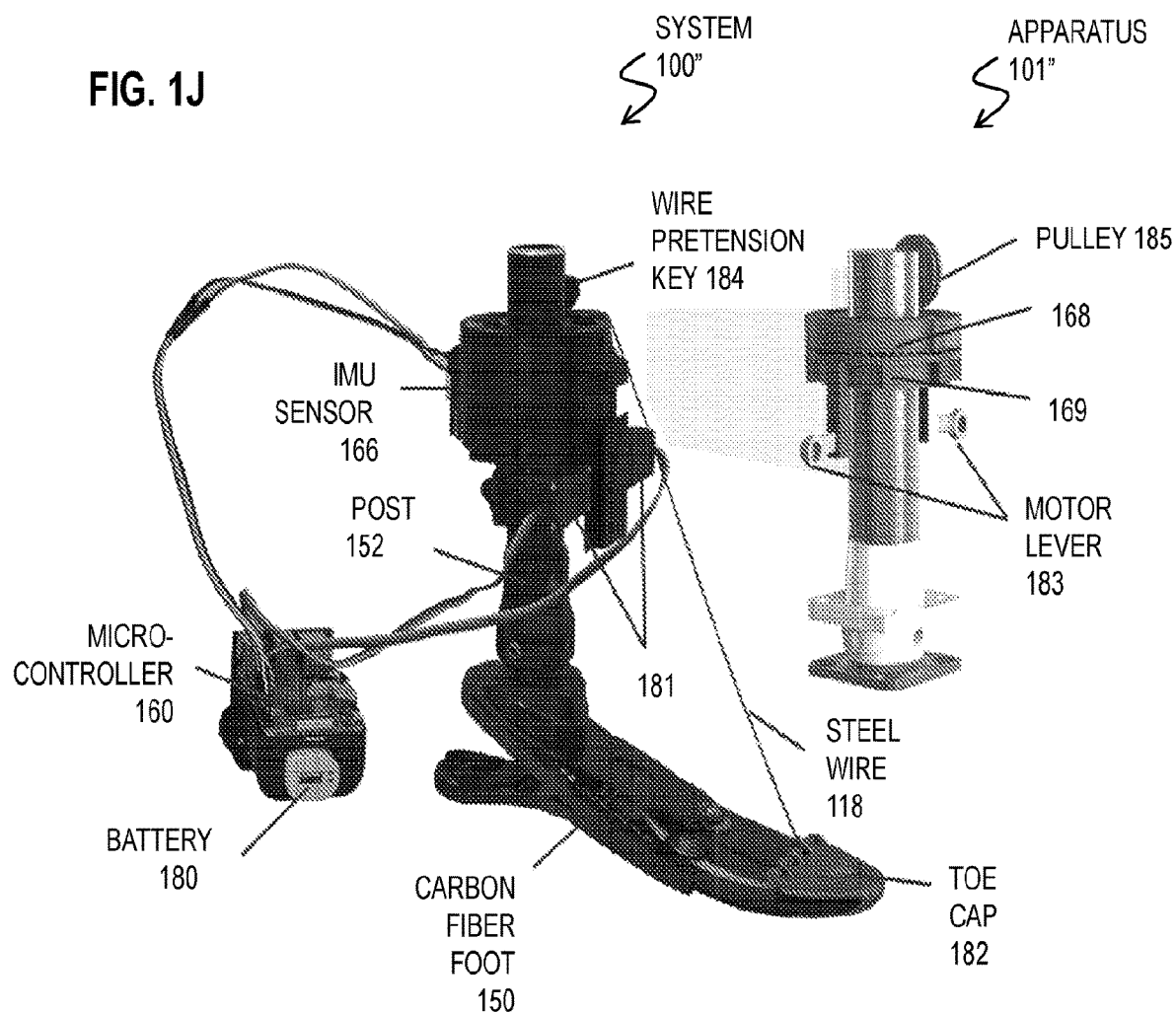
FIG. 1J is an image that illustrates an example of a side perspective view of a system including a leg prothesis with an apparatus mounted thereon, according to an embodiment.

FIG. 1J is an image that illustrates an example of a side perspective view of a system 100" including a leg prothesis 151 with an apparatus 101" mounted thereon, according to an embodiment. In an embodiment, the system 100" and apparatus 101" are similar to the system 100' and apparatus 101' discussed above, with the exception of the features discussed herein. In an embodiment, a toe cap 182 is connected to the leg prothesis 151 (e.g. carbon fiber foot 150) and is used to connect the leg prothesis 151 (e.g. with the wire 118) to the ratchet gear 168, 169. In an example embodiment, the toe cap 182 is a universal prosthetic toe cap that can fit to most of current standard of care passive ankle prostheses. In an embodiment, the apparatus 101" includes a wire pretension key 184 to provide pretension to the wire 118. In an embodiment, the apparatus 101" includes servo motors 181 (e.g. two servo motors) to disengage the ratchet gears 168, 169 and provide the propulsion along the direction of travel 212 (e.g. moving from the first gait phase to the second gait phase). In an example embodiment, to control the energy release timing, the microcontroller 160 is provided (e.g. Raspberry Pi 3B, Raspberry Pi, UK) and is powered by a battery 180. In an example embodiment, the microcontroller 160 receives signals that indicate acceleration from the IMU sensor 166 (e.g. LSM9DS1D Adafruit, New York, NY).

The inventors recognized that while the typical range of motion of an unimpaired ankle in dorsiflexion is around 10–20° (e.g. angle 208 in FIG. 2B), walking with stiff passive ankle prostheses can lead to a smaller ankle dorsiflexion angle. The inventors further recognized that such a small ankle dorsiflexion angle may be inadequate to rotate the ratchet gear (e.g. upper and lower ratchet gears 168, 169) from the third gait phase to the first gait phase (e.g. rotate the ratchet gear from the first angle 216 to the second angle 216' in FIGS. 2E-2F). Thus, to amplify the amount of possible deformation on the system 100", the first end of the wire 118 (e.g. a Kevlar string) is attached to the toe cap 182 designed to fit the shape of a leg prosthesis 151 and the second end of the wire 118 is attached at a top section of the apparatus 101" (e.g. to a pulley 185 at the top section of the apparatus 101", see FIG. 1J). In an embodiment, the amount of wire 118 retraction is related to the ankle angle (e.g. angle 208), either when the prosthetic 151 is at rest or when the prosthetic 151 is at the desired dorsiflexion. Thus, in one example embodiment, for small ankle dorsiflexion angle (e.g. where the angle 208 is less than 10 degrees), the pulley 185 magnifies the rotation of the ratchet gear (e.g. upper and lower ratchet gears 168, 169) such that the ratchet gear rotates from the first angle 216 to the second angle 216' (FIGS. 2E-2F). In an example embodiment, the pulley 185 is rotatably coupled to the ratchet gears and causes the ratchet gears to rotate by a magnified angle (e.g. based on a dimension of the pulley 185) that the ratchet gears would not have rotated if the wire 118 was connected to the ratchet gears.

In addition to the variability in the ankle dorsiflexion angle, the inventors recognized that there is variability among transtibial amputees, in terms of the length of the post 152 from the residual limb (e.g. longer post 152 for individuals with shorter residual limb, shorter post 152 for individuals with longer residual limb, etc.) The inventors similarly recognized that the ratchet gear alone cannot accommodate this variability as different distances between the toe (e.g. toe cap 182) and the ratchet gears would require a different gear ratio to precisely capture the deformation of the foot. To solve this issue, the pulley 185 was added to the system 100", to amplify the deformation of the foot, allowing the ratchet 168, 169 to rotate a larger amount. In an example embodiment, because of the pulley 185, the range of post 152 length can be extended without having to make a custom set of gears for individuals with different residual limb lengths.

FIG. 3 is a flow chart that illustrates an example method 300 for mounting the apparatus 101, 101' to the system 100, 100' of FIG. 1A, 1F and/or using the system, according to an embodiment. Although steps are depicted in FIG. 3 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, a cable is attached to leg protheses worn by a subject to be moved through a plurality of gait phases 200. In an embodiment, in step 301 the steel wire 118 is attached to a foot portion (e.g. carbon fiber foot 150) of the leg protheses 151. In an example embodiment, in step 301 one or more wire guides 119 are secured along the carbon fiber foot 150 and the steel wire 118 is passed through the wire guides 119. In another example embodiment, the steel wire 118 is attached to a front portion of the carbon fiber foot 150 based on a front side of the subject and/or a forward direction 212 of travel of the subject. In some embodiments, a plurality of steel wires (e.g. four steel wires 118a-118d) are attached to the foot portion of the leg protheses.

In step 302, a module 103, 103' is attached to the leg protheses. In an embodiment, in step 302 the module 103 is attached to the post 152 secured to the leg protheses 151. In some embodiments, in step 302, the module 103, 103' is attached to the post 152 using any conventional means (e.g. screw, nuts and bolt, etc.).

In step 304, the cable attached to the leg protheses in step 301 engages a tension spring (e.g. through the gear) of the module 103 attached to the leg protheses in step 302. In an embodiment, in step 304 after a first end of the steel wire 118 is attached to the carbon fiber foot 150, a second end of the steel wire 118 opposite to the first end engages the gear 112 and tension spring 114 of the module 103. In another embodiment, in step 304 a second end of the steel wires 118a-118d engage the lower ratchet gear 169 and tension spring 114' of the module 103'. In an example embodiment, in step 304 the steel wire 118 is engaged with the tension spring 114 so that the tension spring 114 maintains a minimum amount of tension in the steel wire 118 through each gait phase 202 of the plurality of gait phases 200. In an example embodiment, various components of the system 100 such as the springs and gears include one or more dimensions or parameters similar to those provided by McMaster Carr® of Elmhurst Illinois. In some embodiments, in step 304 the steel wires 118a-118d are passed through the respective openings 121a-121d adjacent a base of the apparatus 101' and/or to a respective wire guide pole 170 after which the steel wires 118a-118d are attached to respective portions of the lower ratchet gear 169.

In step 305, the post 152 pivots relative to the leg prothesis 151 (e.g. from the first axis 210 to the second axis 210') and the gear and rotational tension spring rotate in the first direction (e.g. clockwise direction 218) so that a length of the cable varies between the third gait phase (e.g. 30% gait phase 202c) and first gait phase (e.g. 50% gait phase 202e). In an embodiment, in step 305 the length of the cable varies by the steel wire 118 retracting in direction 206 into the module 103, 103' such that the length of the steel wire 118 is shortened between the third and first gait phases. In an example embodiment, in step 305 the gear 112 and rotational tension spring 114 rotate in the first direction so that the steel wire 118 retracts in direction 206 into the module 103 and the rotational tension spring 114 maintains tension in the steel wire 118. In another example embodiment, in step 305 the lower ratchet gear 169 rotates relative to the upper ratchet gear 168 in the first direction so that the steel wires 118a-118d retract in direction 206 into the module 103' and the rotational tension spring 114' maintains tension in the steel wires 118a-118d.

In step 306, a position of the gear 112 and rotational tension spring 114 is fixed with the locking mechanism to maintain a length of the cable between the module 103 and leg prosthesis 151 during the first gait phase (e.g. 50% gait phase 202e). In an embodiment, in step 306 the position of the gear 112 and rotational tension spring 114 is fixed by the pawl 110 engaging the gear 112 to maintain the length of the steel wire 118 between the module 103 and the carbon fiber foot 150 during the first gait phase (e.g. 50% gait phase 202e). In an embodiment, in step 306 the sensor 106 measures data indicating the current gait phase and transmits this data to the controller 102. In this embodiment, the controller 102 compares the data indicating the current gait phase with data stored in the memory 108 indicating the second gait phase (e.g. 60% gait phase 202f) and since the current gait phase does not match the second gait phase, the controller 102 does not transmit a signal to the servo motor 104 and pawl 110 to cause the pawl 110 to disengage the gear 112. In other embodiments, step 306 involves a position of the lower ratchet gear 169 and rotational tension spring 114' being fixed with the locking mechanism (e.g. upper ratchet gear 168, compression spring 164) to maintain the length of the steel wires 118a-118d between the module 103' and the leg prosthesis during the first gait phase.

In step 308, a position of the gear 112 and rotational tension spring 114 is released with the locking mechanism to permit variation to the length of the cable between the module 103 and leg prosthesis 151 during a second gait phase (e.g. 60% gait phase 202f). In an embodiment, in step 308 the position of the gear 112 and rotational tension spring 114 is unlocked by the pawl 110 disengaging the gear 112 to permit variation of the length of the steel wire 118 between the module 103 and the carbon fiber foot 150 during the second gait phase (e.g. 60% gait phase 202f). In an embodiment, in step 308 the sensor 106 measures data indicating the current gait phase and transmits this data to the controller 102. In this embodiment, the controller 102 compares the data indicating the current gait phase with data stored in the memory 108 indicating the second gait phase (e.g. 60% gait phase 202f) and since the current gait phase matches the second gait phase, the controller 102 transmits a signal to the servo motor 104 and pawl 110 to cause the pawl 110 to disengage the gear 112. In other embodiments, step 308 involves a position of the lower ratchet gear 169 and rotational tension spring 114' being released with the locking mechanism (e.g. upper ratchet gear 168, compression spring 164) to permit variation of the length of the steel wires 118a-118d between the module 103' and the leg prosthesis 151 during the second gait phase.

In an embodiment, the release timing of step 308 is based on a percentage of the gait cycle (e.g. 60% second gait phase 202f). In one example embodiment, the release timing of step 308 is measured by the gait of the user instead of a set time after each heel strike (effectively pushing the user to toe off at a set time). In one example embodiment, the system is calibrated for each individual user, by initially recording the gait cycle for each user and determining a time gap between consecutive heel strikes (e.g. the controller 102 measures the time gap between peak acceleration data received from the IMU sensor 166). In this example embodiment, the controller 102 then determines the release timing for step 308 based on a fixed percentage value (e.g. 60% gait phase 202f) of this determined time gap. In one example embodiment, if the controller 102 determines a time gap of 3 seconds (e.g. based on the time gap between peak acceleration values from the IMU sensor 166), then the controller 102 calculates the release timing of step 308 based on 60% of this value (e.g. about 1.8 seconds after each heel strike). In an example embodiment, the controller 202 performs step 308 based on releasing the locking mechanism after the determined time gap (e.g. 1.8 seconds) following the most recent heel strike (e.g. peak acceleration signal received from the IMU sensor 166). In still further embodiments, the controller 102 continuously records the time gap (e.g. between heel strikes) as the user walks and thus continuously updates the time gap used for release timing in step 308. This advantageously ensures that the release timing of step 308 remains accurate, despite the user varying their walking speed (e.g. since the release timing is based on the time gap between heel strikes of the immediately preceding gait cycle).

In one embodiment, the release of the energy in step 308 is controlled by the controller 102, such as the microcontroller 160 (e.g. Raspberry pi 3B, Raspberry Pi, UK) that constantly checks signals from the IMU sensor 166 (e.g. LSM9DS1D Adafruit, New York, NY) to identify heel strikes. In this example embodiment, the signal received at the microcontroller 160 from the IMU sensor 166 indicates the magnitude of the acceleration data. Once the release timing of step 308 is obtained the microcontroller 160 sends a signal out to the controlling servos 181 to release the ratchet gears and allow the ankle prosthetic to release its deformation, returning energy into the gait. Once a new heel strike is detected the microcontroller sends a signal to the servos to reengage the ratchet, allowing springs to maintain contact between the gear teeth.

The inventors recognized that passive ankle prostheses are generally rated to hold up to a maximum weight (e.g. 136 kg). In an embodiment, the inventors used this maximum weight value to validate the stress on the ratchet gear of the system. In one embodiment, the maximum weight value is used to evaluate whether the ratchet gears can handle the stress which is induced by the passive prosthesis deformation. The inventors recognized that two actions are to be evaluated, which include the ability to recoil the wire while preventing extraction, and the release of the gears at a decided moment (e.g. 60% gait phase 202*f*), allowing the wire to return to its previous length. In an example embodiment, the system was tailored to work with a specific ankle prosthesis (e.g. LP Vari-Flex, Ossur) and a titanium post/ pylon (e.g. length of about 89 mm). Various tests were used to verify the viability of the system.

Figure 7A:
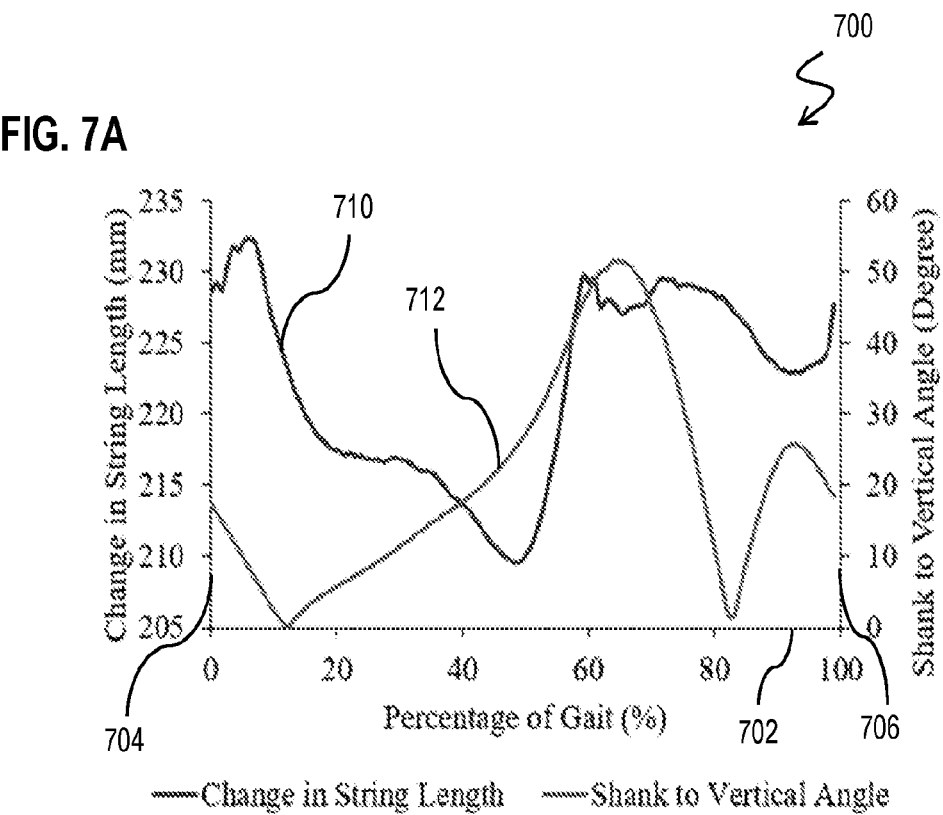
FIG. 7A is a graph that illustrates an example of curves that indicate a change in wire length and shank to vertical angle, according to an embodiment.
Figure 7B:
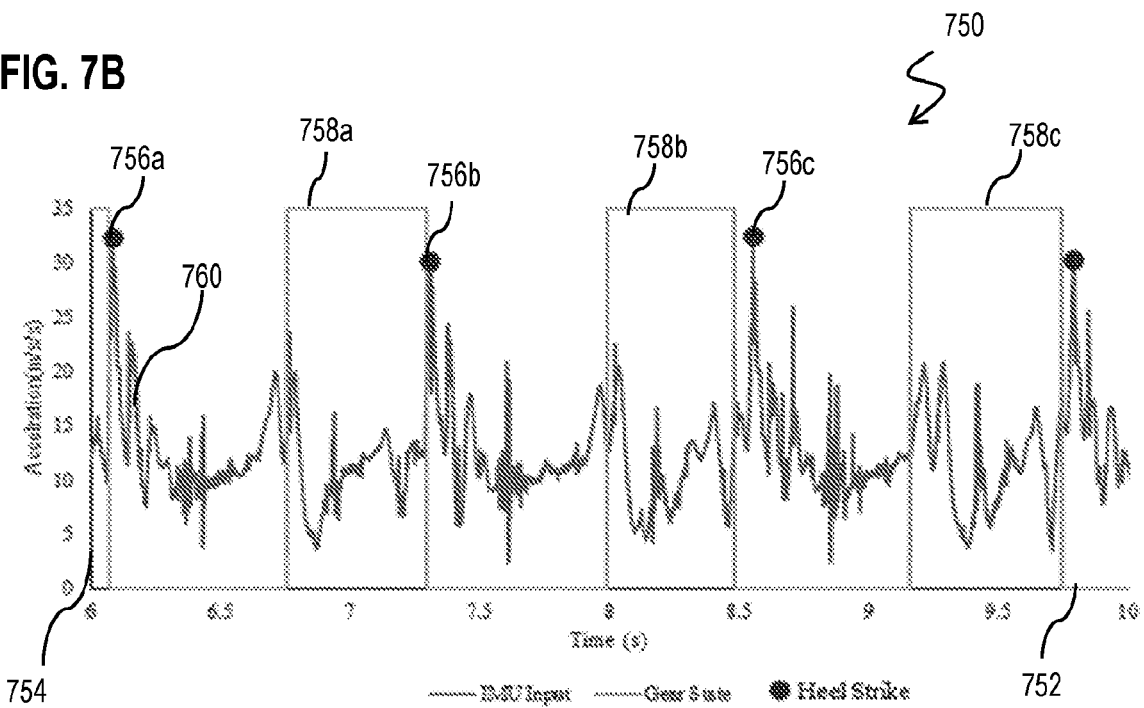
FIG. 7B is a graph that illustrates an example of a curve indicating an input of the IMU sensor to the controller over multiple gait cycles, according to an embodiment.

In one embodiment, a first test was performed for IMU sensor and controller (microprocessor) validation. The system was tested by attaching the micro controller to an unimpaired individuals shank during walking. The accelerometer data from IMU sensor was plotted against the actuating signal of the microprocessor (e.g. to ensure that the controller transmits the signal to release the locking mechanism at the appropriate time, such as 60% gait phase 202*f*). The microcontroller was set to have a minimum threshold of 18 m/second$^2$ for heel strike recognition and a release timing of 57% of previous gait. These example values of the threshold acceleration and release timing are merely one example embodiment and do not limit the embodiments of the present invention. FIG. 7B is a graph 750 that illustrates an example of a curve 760 indicating an input of the IMU sensor to the controller over multiple gait cycles, according to an embodiment. The horizontal axis 752 is time in units of seconds. The vertical axis 754 is acceleration in units of meters per second$^2$. Peak values 756*a* through 756*c* along the curve 760 indicate heel strike instances based on the maximum acceleration value of the curve 760. In an embodiment, the boxed regions 758*a* through 758*c* indicate the time regions during which the locking mechanism releases the ratchet gears in step 308 (e.g. starting at about 60% gait phase 202*f*). In another embodiment, the boxed regions 758 end at about the heel strike gait phase (peak values 756 in FIG. 7B). In one embodiment, FIG. 7B demonstrates that the system will allow the prosthetic to deform back after a selected time and the system will only allow the wire to recoil after the next successive heel strike.

Figure 6A:
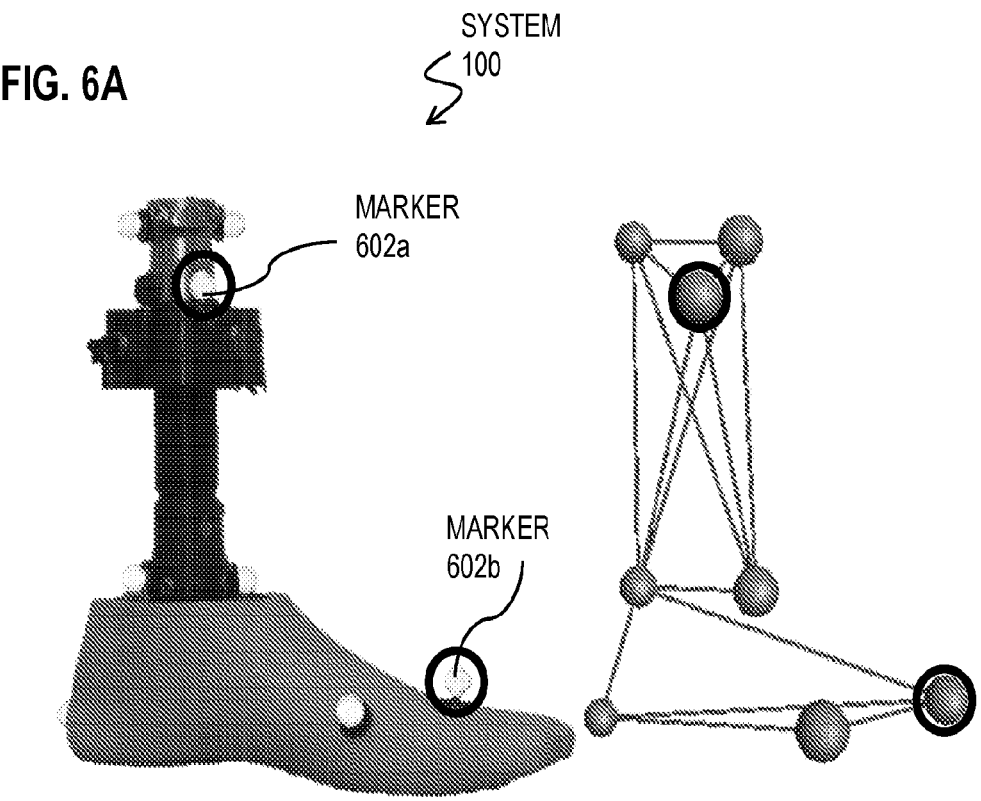
FIG. 6A is an image that illustrates an example of a side view of the system of FIG. 1A with reflective markers used in a motion capture system, according to an embodiment.

In an embodiment, a second test was performed of prosthetic deformation. In this test, the prosthetic ankle was worn by a volunteer after being fitted by a prosthetist. FIG. 6A is an image that illustrates an example of a side view of the system 100 of FIG. 1A with reflective markers 602*a*, 602*b* used in a motion capture system, according to an embodiment. In one example embodiment, a plurality (e.g. nine) reflective motion capture markers 602 (e.g. Pearl Markers, B&L Engineering) were placed on the prosthesis (carbon fiber foot 150), the post 152 and the apparatus 101. In one example embodiment, the position of the markers 602 were captured using a camera system (e.g. Vicon system with twelve cameras). In an example embodiment, a length between two markers 602*a*, 602*b* was calculated corresponding to an estimated length of the wire 118 based on the length between the wire attachment points (e.g. toe cap 182 and pulley 185).

In an example embodiment, during the second test, the prosthetic total deformation was measured to be about 23 mm. FIG. 7A is a graph 700 that illustrates an example of curves 710, 712 that indicate a change in wire length (curve 710) and shank to vertical angle (curve 712), according to an embodiment. The horizontal axis 702 is percentage of the gait in units of percentage (e.g. measured from the heel strike phase). The left vertical axis 704 indicates a length of the wire (in units of mm). The right vertical axis 706 indicates a shank to vertical angle in units of degrees. In an embodiment, the foot deformation was measured by looking at the toe and string attachment markers 602*a*, 602*b*. Since the prosthesis used was donated, the stiffness was high for the user creating less dorsiflexion. Additionally, the volunteer was out-toeing during walking reducing the overall deformation (see FIG. 7A).

Figure 6B:
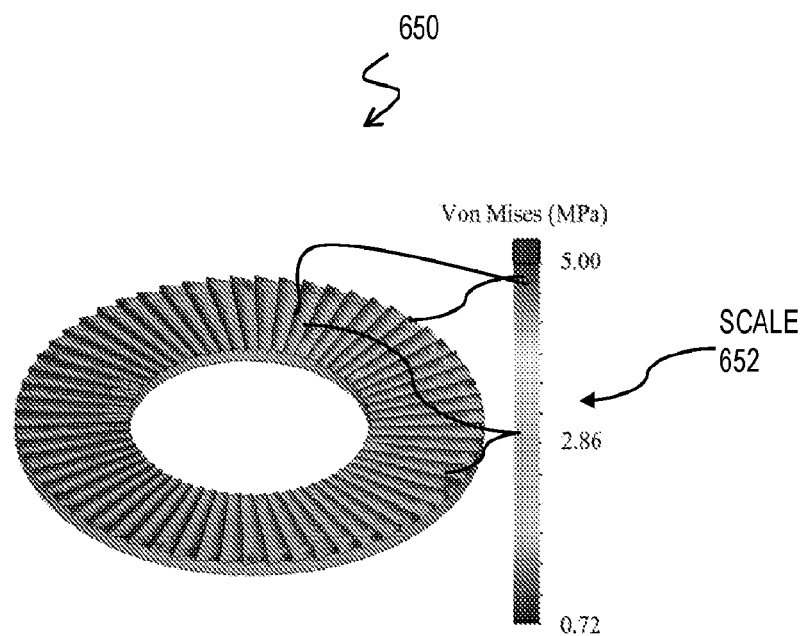
FIG. 6B is an image that illustrates an example of a top perspective view of a stress analysis on teeth of the ratchet gear of the system of FIG. 1G, according to an embodiment.

In an embodiment, a third test was performed of gear stress analysis. In one example embodiment, the predicted von mises stress on the fully loaded gears was modeled using finite element analysis (e.g. SolidWorks, Dassault Systems Concord, MA) to get a base estimate of the stress that the system could have on the gears. FIG. 6B is an image that illustrates an example of a top perspective view of a stress analysis 650 on teeth of the ratchet gear of the system 100' of FIG. 1G, according to an embodiment. A scale 652 is provided that indicates different values of the von mises stress (in units of megapascal or Mpa). The finite element analysis simulation result showed the maximum von mises stress presented on the gear teeth was about 5 MPa, suggesting that the level of stress is lower than the yield stress of many light material such as aluminum and fortified plastic.

In an embodiment, a fourth test was performed of gear movement. In one embodiment, while the system was secured to a bench, the wire was pulled by a certain distance (e.g. 15 mm) and the rotation of the gear during extraction and retraction was measured, in order to determine the resolution of the deformation capturable, defined by the gear teeth. When the wire was pulled by the maximum deformation (e.g. 15 mm manually), the total rotation of the ratchet was about 90°. As each gear tooth expands 6°, the resolution of the system is 1 mm of deformation. These numerical values are merely one example embodiment of parameter values of the system and thus the system can be designed with other parameter values.

In healthy individuals, activation of the gastrocnemius typically occurs around 50% of the gait cycle. The longitudinal ground reaction force occurs around 55% of the gait cycle. This suggests that activity pattern of gastrocnemius is not directly related to push off from the foot. Another factor to consider is the variable amount of force required in push off. People with transtibial amputation normally do not have control over either of these variables with a passive ankle prosthesis. The ability to set the energy release timing to a given percentage of the gait cycle is possible with the addition of the system discussed herein. Since the system works based on the walking speed of the individual, the system can be controlled by the user. With this achievement, control of the system with the walking speed, the mimicry of the gastrocnemius is partially achieved, i.e. the timing is controlled, but not the magnitude of the delivered force.

In an embodiment, the system augmentation can achieve some of the functionality of a power prosthesis onto a passive device without the disadvantages found in powered devices such as increased weight and bulkiness. On average, a powered prosthesis weighs around 2.4 kg. The stress observed in the gears through the finite element analysis was low and with the correct design and proper lubrication the gears should bear most of the stress. As result, the device can be made from lightweight materials (e.g. aluminum or tough plastics such as Nylon). This allows the system to minimally change the weight of the prosthesis, maintaining the metabolic efficiency of the system. In one example embodiment, the system weighs about 0.49 kg or in a range from about 0.3 kg to about 0.5 kg, and the weight of a typical passive ankle prostheses is approximately 0.8 kg, suggesting both weights will not greatly negatively impact the metabolic cost of gait. Another advantage of the system's light weight is that even if the power were to be completely off, the gears' wire only needs to be loosened to allow the prosthesis to work as a passive device. By decreasing the dependency on the life of a battery, the user does not need to constantly worry about recharging the device.

In one example embodiment, a skewed weight distribution is commonly observed in recently developed prosthesis control units, leading to the generation of undesired joint torque and gait asymmetry during walking. Besides having a lightweight device, a major emphasis was placed in maintaining the cylindrical symmetry of the weight distribution. In one example embodiment, the prosthetic timing module was designed with a vertical ratchet system to redistribute the force and weight. Two servo motors and the gears were placed vertically along the longitudinal centerline of the pylon of the prosthesis resulting in an evenly distributed mass on the shank. This design has a similar center of mass and moment of inertia properties to the intact shank of an unimpaired individual, potentially improving gait asymmetry and metabolic cost. If it is necessary to adjust the center of mass or moment of inertia of the device, the height of the timing module can be adjusted, so that these properties have the best outcome for walking.

In an example embodiment, although the passive ankle prostheses emulates a mechanism of the gastrocnemius and Achilles tendon to generate plantarflexion torque, the level of plantarflexion torque and ankle power is less than that of a biological ankle because passive ankle prostheses have no power generating source, a role formerly held by the musculature. In an example embodiment, the system can be altered by adding a motor to the pulley, allowing it to further deform the prosthetic if necessary, effectively converting the system into a powered prosthesis. By adding this second parameter, walking stability and consistency can be improved further when accelerations or decelerations are required.

In one embodiment, the methods for predicting the optimal energy release timing can also be further enhanced. In an example embodiment, one potential way to control the ankle prosthetic timing module include an electromyography (EMG) signal from the residual gastrocnemius. While most plantar flexors are removed (including the soleus) from the traumatic surgery of transtibial amputation, only the gastrocnemius muscle is spared and is generally used for wrapping around the distal wounded area to provide cushioning during walking. The activation patterns of the affected gastrocnemius vary greatly between people with transtibial amputation, but some have similar activation patterns as those of unimpaired individuals during walking. The EMG signal from these affected gastrocnemii can provide insight on the control of the energy release timings of these passive ankle prostheses.

In an example embodiment, another potential way to control the ankle prosthetic timing module involves an IMU sensor signal from a body segment. In an example embodiment, there are many different walking conditions such as inclines, declines, stairs, and turns in daily living. In this example embodiment, using signals from an IMU sensor can provide appropriate energy release timings in different walking conditions.

In an example embodiment, another potential way to control the ankle prosthetic timing module involves measuring rotation of the gear. In this example embodiment, the rotation of the ratchet gear is proportional to the amount of deformation of the prosthesis. By measuring the rotation of the ratchet gear, the amount of energy stored by the passive ankle prosthesis can be estimated during walking.

In an example embodiment, another potential way to control the ankle prosthetic timing module involves a Machine Learning Algorithm. In this example embodiment, walking is a complex dynamic movement that varies among individuals in terms of both walking pattern and speed. By developing a system that learns from how a certain individual move under different conditions, both the device and the person can adapt to each other. This implementation can make the system more robust as well as facilitate new users attempting to use device.

In an example embodiment, additional designs can be developed that focus on investigating how different energy releasing timings contribute to human body propulsion and identifying the relation between optimal energy release timing, which maximizes the acceleration of propulsion, and the activity of the affected gastrocnemius muscle in a full clinical study. These outcomes will provide insights for developing control algorithms which can determine the optimal energy release timing.

Figure 4:
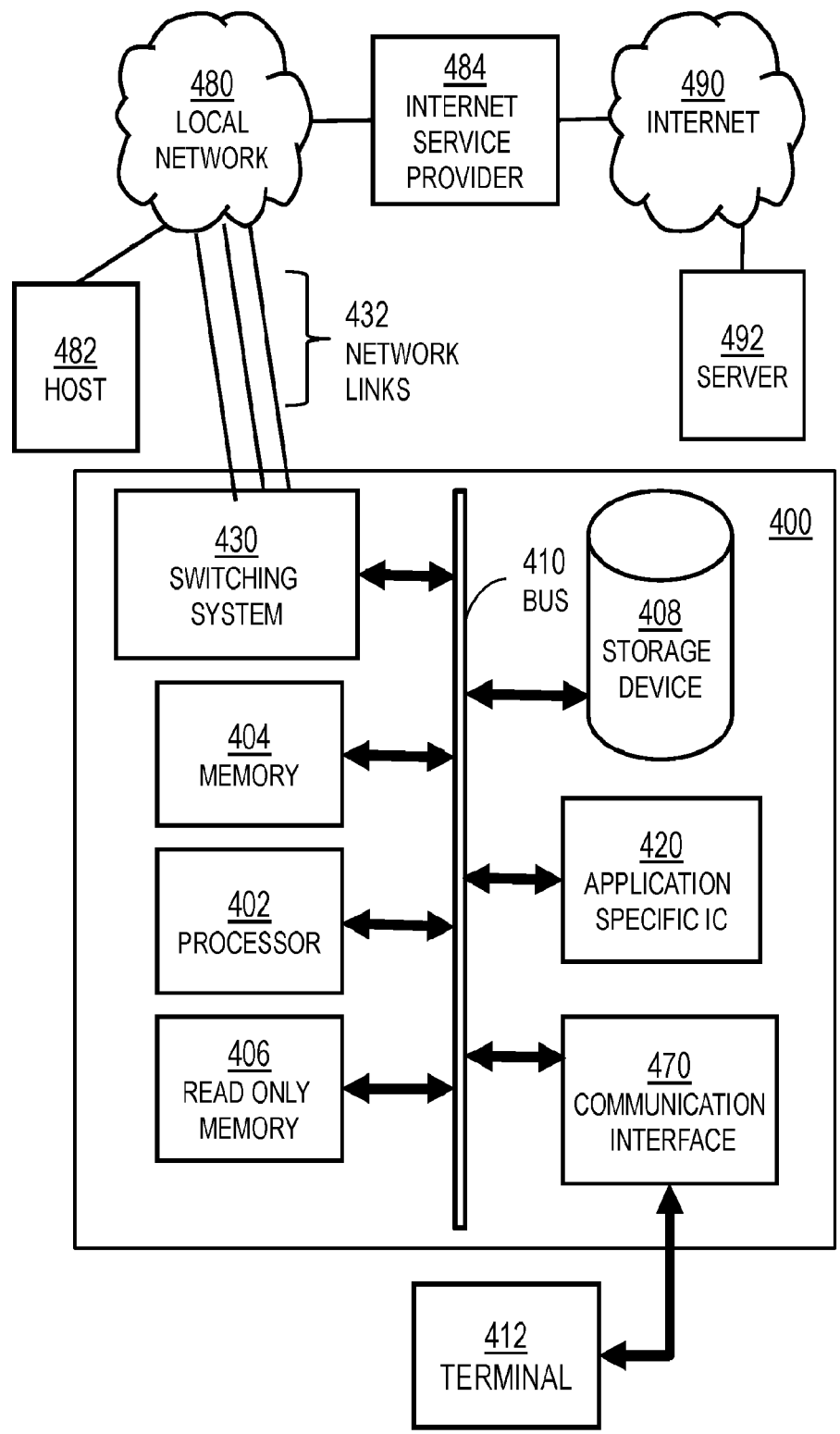
FIG. 4 is a block diagram that illustrates a computer system upon which an embodiment of the invention may be implemented.

The embodiments of the present invention demonstrate that the ankle prosthetic timing module can improve walking for people with transtibial amputation by providing an appropriate energy release timing that can improve propulsion of body during walking. The system is compact, lightweight, and adaptable, enabling it to be installed onto most current standard of care passive ankle prostheses. In one embodiment, its design allows for the adjustment of the moment of inertia of the shank, further increasing its adaptability in order to help improve walking function more broadly among the population of transtibial amputees 2. Hardware Overview FIG. 4 is a block diagram that illustrates a computer system 400 upon which an embodiment of the invention may be implemented. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 400, or a portion thereof, constitutes a means for performing one or more steps of one or more methods described herein.

A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitutes computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 470 sends and receives electrical, acoustic or electromagnetic signals, including infrared and optical signals, that carry information streams, such as digital data.

The term computer-readable medium is used herein to refer to any medium that participates in providing information to processor 402, including instructions for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 402, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 402, except for carrier waves and other signals.

Logic encoded in one or more tangible media includes one or both of processor instructions on a computer-readable storage media and special purpose hardware, such as ASIC *420.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, carry information to and from computer system 400. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received, or may be stored in storage device 408 or other non-volatile storage for later execution, or both. In this manner, computer system 400 may obtain application program code in the form of a signal on a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to a signal on an infra-red a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

Figure 5:
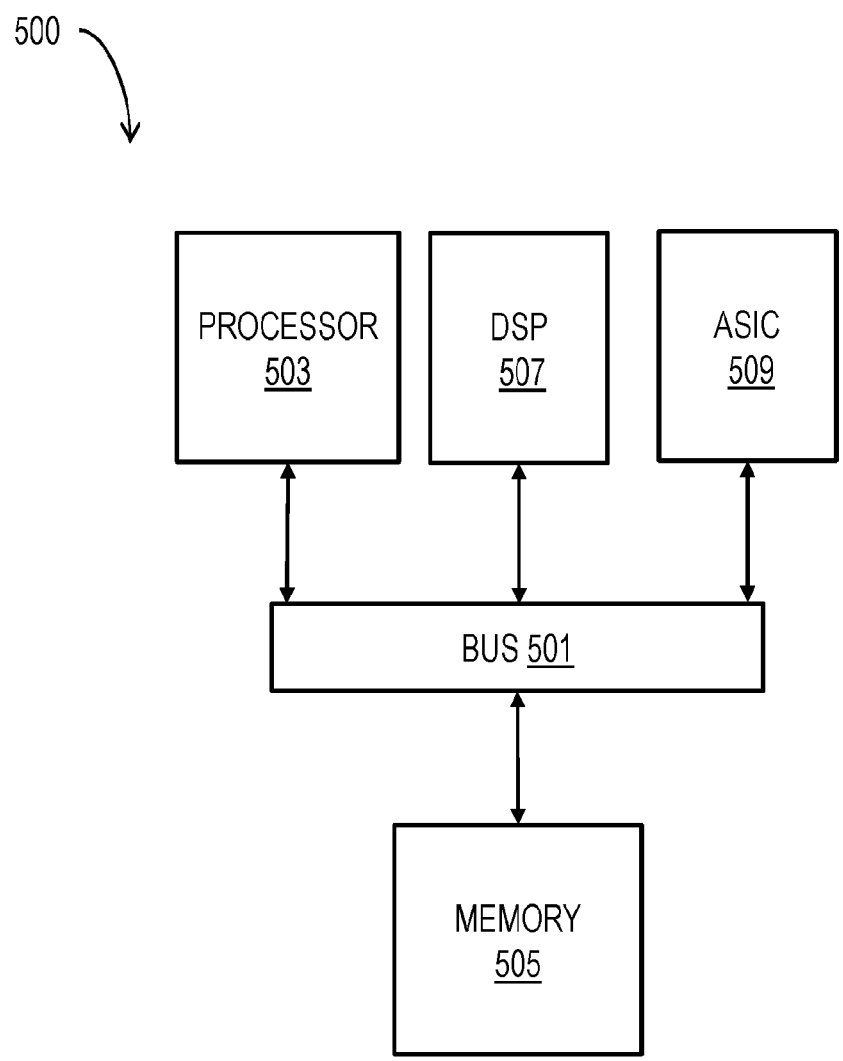
FIG. 5 illustrates a chip set upon which an embodiment of the invention may be implemented.

FIG. 5 illustrates a chip set 500 upon which an embodiment of the invention may be implemented. Chip set 500 is programmed to perform one or more steps of a method described herein and includes, for instance, the processor and memory components described with respect to FIG. *4 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 500, or a portion thereof, constitutes a means for performing one or more steps of a method described herein.

In one embodiment, the chip set 500 includes a communication mechanism such as a bus 501 for passing information among the components of the chip set 500. A processor 503 has connectivity to the bus 501 to execute instructions and process information stored in, for example, a memory 505. The processor 503 may include one or more processing cores with each core configured to perform independently. A multi-core processor enables multiprocessing within a single physical package. Examples of a multi-core processor include two, four, eight, or greater numbers of processing cores. Alternatively or in addition, the processor 503 may include one or more microprocessors configured in tandem via the bus 501 to enable independent execution of instructions, pipelining, and multithreading. The processor 503 may also be accompanied with one or more specialized components to perform certain processing functions and tasks such as one or more digital signal processors (DSP) 507, or one or more application-specific integrated circuits (ASIC) 509. A DSP 507 typically is configured to process real-world signals (e.g., sound) in real time independently of the processor 503. Similarly, an ASIC 509 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 503 and accompanying components have connectivity to the memory 505 via the bus 501. The memory 505 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 505 also stores the data associated with or generated by the execution of one or more steps of the methods described herein.

3. Alternatives, Deviations and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. An apparatus comprising:
    a cable including a first end of the cable configured to be attached to a front portion of a leg prosthesis worn by a subject to move through a plurality of gait phases, wherein the front portion of the leg prothesis faces a front side of a subject wearing the leg prothesis;
    a module configured to be mounted to the leg prosthesis, wherein the module comprises;
        a tension spring configured to engage a second end of the cable to maintain tension in the cable, wherein the second end of the cable is opposite to the first end of the cable, and
        a locking mechanism configured to lock a position of the tension spring and maintain a length of the cable defined between the module and the front portion of the leg prosthesis during a first gait phase of the plurality of gait phases and configured to unlock the position of the tension spring to permit variation of the length of the cable during a second gait phase of the plurality of gait phases;
    wherein the apparatus is configured such that the length of the cable extending from the module to the front portion of the leg prothesis is increased during the second gait phase comprising a toe off gait phase during plantarflexion.

2. The apparatus of claim 1, wherein the module further comprises a gear movably coupled to the tension spring, wherein the locking mechanism is further configured to engage the gear to lock the position of the gear and the tension spring and wherein the locking mechanism is further configured to disengage the gear to unlock the position of the gear and tension spring.

3. The apparatus of claim 1, wherein the leg prosthesis is a carbon fiber foot and wherein the leg prothesis further comprises a post pivotally coupled to the carbon fiber foot such that the post rotates from a first angle relative to the carbon fiber foot during the first gait phase to a second angle relative to the carbon fiber foot during the second gait phase.

4. The apparatus of claim 1, further comprising at least one cable guide configured to be secured along the leg prosthesis to guide the first end of the cable attached to the front portion of the leg prosthesis.

5. The apparatus of claim 1, wherein the module comprises:
    an inertial measurement unit (IMU) sensor configured to measure data indicating a current gait phase of the plurality of gait phases and further configured to transmit the measured data to a controller;
    a motor operatively connected to the locking mechanism; and
    the controller communicatively coupled with the IMU sensor and the motor, said controller configured to receive the measured data from the IMU sensor indicating the current gait phase and further configured to compare the current gait phase with the first gait phase and the second gait phase;
    wherein the controller is configured to transmit a signal to the motor to lock the position of the locking mechanism upon a determination that the current gait phase is the first gait phase; and
    wherein the controller is configured to transmit a signal to the motor to unlock the position of the locking mechanism upon a determination that the current gait phase is the second gait chase.

6. The apparatus of claim 2, wherein the locking mechanism comprises a pawl to engage the gear to lock the position of the gear during the at least one first gait phase and wherein the locking mechanism further comprises a servo motor to cause the pawl to disengage the gear to unlock the position of the gear during the second gait phase.

7. The apparatus of claim 6, further comprising a sensor to measure a current gait phase of the leg prosthesis and transmit data indicating the current gait phase to the servo motor and wherein the servo motor is configured to cause the pawl to disengage the ratchet gear based on determination that the current gait phase is the second gait phase.

8. The apparatus of claim 2, wherein
    the tension spring is a rotational tension spring configured to rotate based on retraction of the cable into the module to maintain tension in the cable; and
    wherein the gear is a ratchet gear rotatably coupled to the rotational tension spring.

9. The apparatus of claim 8, wherein the locking mechanism comprises a pawl to engage the ratchet gear to lock the position of the ratchet gear during the first gait phase and wherein the locking mechanism further comprises a servo motor to cause the pawl to disengage the ratchet gear to unlock the position of the ratchet gear during the second gait phase.

10. The apparatus of claim 9, wherein the rotational tension spring and ratchet gear are configured to rotate in a first direction from a first angle to a second angle due to retraction of the length of the cable from a first length to a second length based on movement of the leg prothesis from a midstance gait phase to the first gait phase comprising a heel off gait phase during dorsiflexion.

11. The apparatus of claim 10, wherein the pawl is configured to engage the ratchet gear to lock the rotational tension spring and ratchet gear at the second angle during movement of the leg prosthesis during a gait phase between the heel off gait phase and the toe off gait phase.

12. The apparatus of claim 10, wherein the rotational tension spring and ratchet gear are configured to rotate in a second direction opposite to the first direction from the second angle to the first angle due to extension of the length of the cable from the second length to the first length based on movement of the ankle prosthesis during the second gait phase comprising the toe off gait phase during plantarflexion.

13. The apparatus of claim 1, wherein the first gait phase comprises a midstance gait phase or a terminal gait phase and wherein the second gait phase comprises the toe off gait phase.

14. The apparatus of claim 13, wherein the first gait phase comprises the midstance gait phase, the terminal stance gait phase or a gait phase between a heel off gait phase and the toe off gait phase.

15. A method comprising:
    attaching a first end of a cable to a front portion of a leg prosthesis worn by a subject and moved through a plurality of gait phases, wherein the front portion of the leg prothesis faces a front side of a subject wearing the leg prothesis;
    attaching a module to a post secured to the leg prothesis, wherein the module comprises a tension spring, a gear movably coupled to the tension spring, and a locking mechanism;

engaging a second end of the cable with the gear and tension spring of the module to maintain tension in the cable, wherein the second end of the cable is opposite to the first end of the cable;

fixing, with the locking mechanism, a position of the gear and tension spring to maintain a length of the cable defined between the module and the front portion of the leg prosthesis during a first gait phase of the plurality of gait phases; and releasing, with the locking mechanism, the position of the gear and tension spring to vary the length of the cable during a second gait phase of the plurality of gait phases and generate propulsion along a direction of travel of the subject during the at least one second gait phase, said releasing step comprising increasing the length of the cable for the second gait phase comprising a toe off gait phase during plantarflexion.

16. The method of claim 15, wherein the leg prosthesis is a carbon fiber foot and wherein the post is pivotally coupled to the carbon fiber foot such that the moving through the plurality of gait phases comprises rotation of an angle of the post relative to the carbon fiber foot.

17. The method of claim 16, wherein the fixing step comprises maintaining a first angle of the post relative to the carbon fiber foot during the first gait phase and wherein the releasing step comprises varying the angle of the post relative to the carbon fiber foot from the first angle to a second angle after the first gait phase and during the second gait phase.

18. The method of claim 15, further comprising securing at least one cable guide along the leg prothesis and wherein the attaching the cable comprises guiding the cable through the at least one cable guide along the leg prothesis to the front portion of the leg prothesis.

19. The method of claim 15, further comprising;

measuring, with an inertial measurement unit (IMU) sensor, data indicating a current gait phase of the plurality of gait phases;

transmitting, from the IMU sensor, the data indicating the current gait phase to a controller;

receiving, at the controller, the data indicating the current gait phase;

comparing, with the controller, the current gait phase with the first gait phase and the second gait phase;

upon determining that the current gait phase is the first gait phase, transmitting from the controller a signal to a motor to lock the position of the locking mechanism to maintain the length of the cable during the first gait phase; and upon determining that the current gait phase is the second gait phase, transmitting from the controller a signal to the motor to unlock the position of the locking mechanism to permit variation of the length of the cable during the second gait phase.

20. The method of claim 15, wherein the fixing step comprises engaging the gear with a pawl of the locking mechanism to maintain the length of the cable during the first gait phase and wherein the releasing step comprises disengaging, with a servo motor, the pawl from the gear to vary the length of the cable during the second gait phase comprising the toe off gait phase during plantarflexion.

21. A leg prosthesis with the apparatus of claim 1 mounted thereon, wherein the leg prothesis comprises a carbon fiber foot configured to be worn by a subject to replace portions of the leg below the knee after a transtibial amputation.

22. The leg prosthesis of claim 21, wherein the leg prothesis comprises the carbon fiber foot and a post, wherein the first end of the cable is attached to the carbon fiber foot and the second end of the cable is attached to the module is mounted on the post.

\* \* \* \* \*